US012594083B2

(12) United States Patent
Holmes et al.

(10) Patent No.: US 12,594,083 B2
(45) Date of Patent: Apr. 7, 2026

(54) UNIVERSAL BROACH SYSTEM FOR HUMERAL IMPLANTS

(71) Applicant: Zimmer, Inc., Warsaw, IN (US)

(72) Inventors: Cody Johnathon Holmes, Warsaw, IN (US); Michael Mueller, Warsaw, IN (US); Steven E. Stump, Goshen, IN (US)

(73) Assignee: Zimmer, Inc., Warsaw, IN (US)

( * ) Notice: Subject to any disclaimer, the term of this patent is extended or adjusted under 35 U.S.C. 154(b) by 161 days.

(21) Appl. No.: 18/483,140

(22) Filed: Oct. 9, 2023

(65) Prior Publication Data

US 2024/0138854 A1 May 2, 2024

Related U.S. Application Data

(60) Provisional application No. 63/471,883, filed on Jun. 8, 2023, provisional application No. 63/421,829, filed on Nov. 2, 2022.

(51) Int. Cl.
*A61B 17/16* (2006.01)
*A61F 2/40* (2006.01)
(Continued)

(52) U.S. Cl.
CPC ........ *A61B 17/1684* (2013.01); *A61F 2/4003* (2013.01); *A61F 2/4612* (2013.01); *A61B 2017/564* (2013.01)

(58) Field of Classification Search
CPC .... A61F 2/4003; A61F 2/4612; A61F 2/4684; A61F 2002/30607; A61B 17/1659; A61B 17/1684; A61B 17/1778
See application file for complete search history.

(56) References Cited

U.S. PATENT DOCUMENTS

| | | | |
|---|---|---|---|
| 8,512,410 B2 * | 8/2013 | Metcalfe | A61F 2/40 |
| | | | 623/19.14 |
| 9,241,802 B2 * | 1/2016 | Klawitter | A61F 2/4003 |

(Continued)

FOREIGN PATENT DOCUMENTS

| | | |
|---|---|---|
| WO | WO-2007109340 A2 | 9/2007 |
| WO | 2024097504 | 5/2024 |

OTHER PUBLICATIONS

"International Application Serial No. PCT US2023 076360, International Search Report mailed Jan. 18, 2024", 7 pgs.
(Continued)

*Primary Examiner* — Anu Ramana
(74) *Attorney, Agent, or Firm* — SCHWEGMAN LUNDBERG & WOESSNER, P.A.

(57) ABSTRACT

A broach for preparing bone for receiving an anchor for a prosthesis comprises a body comprising a superior surface and a socket extending into the superior surface, and an anchoring component extending from the body comprising a spoke extending laterally from the body and a spoke tip extending proximally from the spoke above the superior surface. A system can comprise a distal broach component comprising a broach body, a socket extending into a superior surface of the broach body, and a plurality of cutting spokes extending radially from the broach body, each of the plurality of cutting spokes separated by an interval pattern, and a proximal broach component comprising a spacer body configured to attach to the superior surface of the broach body, and a plurality of spacer spokes extending radially from the spacer body, each of the plurality of spacer spokes separated by the interval pattern.

12 Claims, 29 Drawing Sheets

(51) Int. Cl.
    *A61F 2/46*       (2006.01)
    *A61B 17/56*     (2006.01)

(56)             References Cited

U.S. PATENT DOCUMENTS

| | | | |
|---|---|---|---|
| 9,498,230 B2 * | 11/2016 | Smith | A61B 17/1617 |
| 11,129,724 B2 * | 9/2021 | Knox | A61F 2/4014 |
| 11,766,335 B2 * | 9/2023 | Knox | A61F 2/4003 |
| | | | 623/19.11 |
| 12,109,121 B2 * | 10/2024 | Knox | A61F 2/4014 |
| 12,295,852 B2 * | 5/2025 | Robicheaux | A61F 2/4003 |
| 2019/0159906 A1 * | 5/2019 | Knox | A61F 2/4003 |
| 2020/0214845 A1 * | 7/2020 | Knox | A61F 2/30767 |
| 2020/0315807 A1 | 10/2020 | Hatzidakis et al. | |
| 2021/0030552 A1 | 2/2021 | Terrill | |
| 2021/0346166 A1 | 11/2021 | Sapio et al. | |
| 2021/0393414 A1 | 12/2021 | Robicheaux et al. | |
| 2022/0175544 A1 | 6/2022 | Ball et al. | |
| 2022/0233322 A1 | 7/2022 | Knox et al. | |

OTHER PUBLICATIONS

"International Application Serial No. PCT US2023 076360, Written Opinion mailed Jan. 18, 2024", 7 pgs.
"International Application Serial No. PCT US2023 076360, International Preliminary Report on Patentability mailed May 15, 2025", 9 pgs.

* cited by examiner

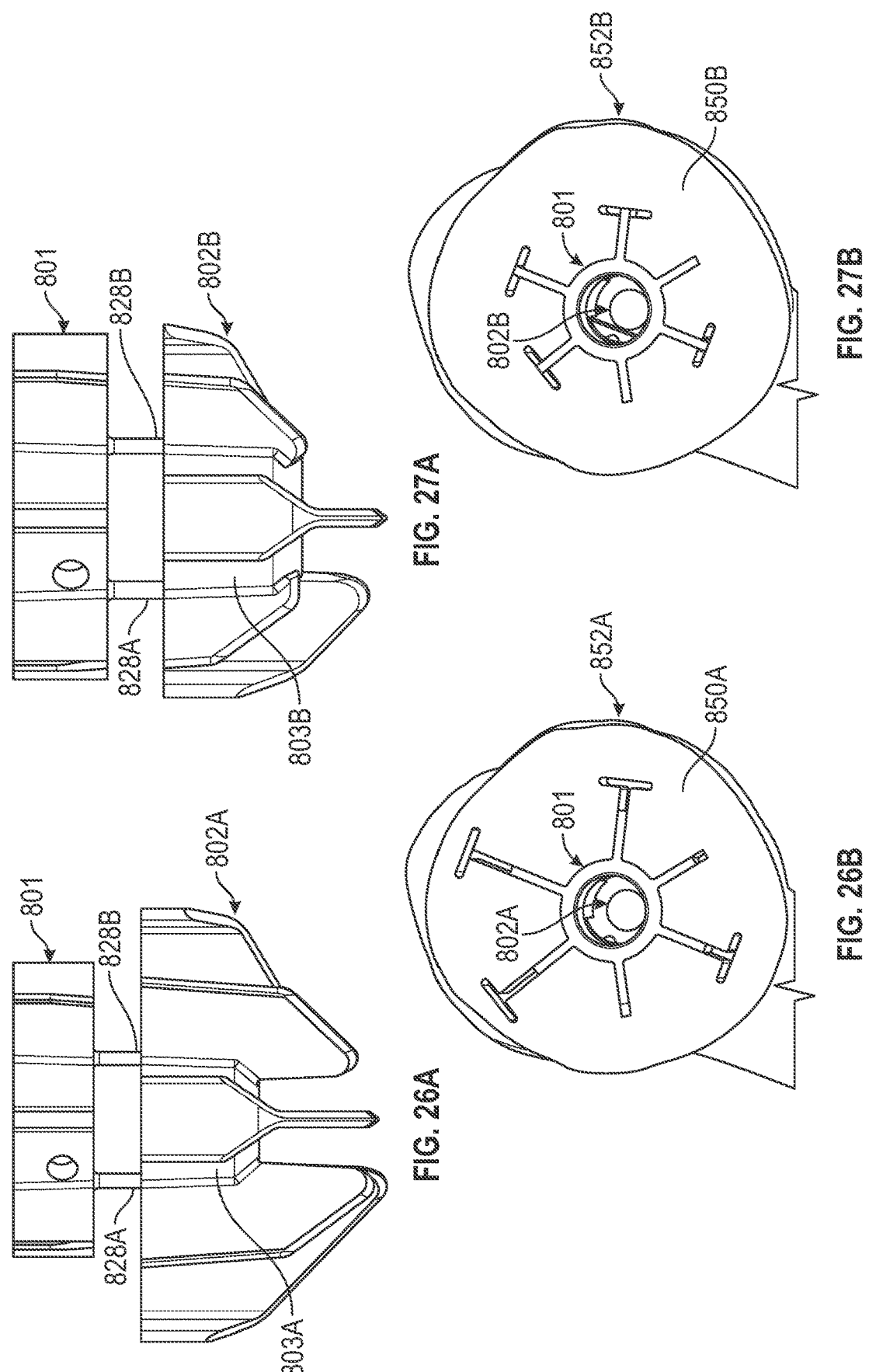

UNIVERSAL BROACH SYSTEM FOR HUMERAL IMPLANTS

CLAIM OF PRIORITY

This application claims the benefit of U.S. Provisional Patent Application Ser. No. 63/421,829, filed on Nov. 2, 2022, and also claims the benefit of U.S. Provisional Patent Application Ser. No. 63/471,883, filed on Jun. 8, 2023, the benefit of priority of which is claimed hereby, and each of which is incorporated by reference herein in its entirety.

TECHNICAL FIELD

The present disclosure is generally directed to, but not by way of limitation, systems, devices and methods for performing medical procedures, such as partial and total shoulder arthroplasties. More specifically, but not by way of limitation, the present disclosure is directed to medical instruments used to perform reverse shoulder arthroplasties, such as broaches used to shape bone to receive a bone anchor.

BACKGROUND

The shoulder joint includes a humerus bone and a scapula bone, which cooperate to provide range of motion of the humerus relative to the scapula during movement of a human arm. Specifically, a proximal end of the humerus including a humeral head is disposed adjacent to a glenoid fossa of the scapula and is permitted to move relative to the glenoid fossa to provide a range of motion to the humerus relative to the scapula.

Joint replacement surgery such as a partial or total shoulder arthroplasty may be required or desired when the shoulder joint causes pain during use or is otherwise damaged. For example, the shoulder joint may be damaged due to osteoarthritis, whereby progressive wearing away of cartilage results in bare bone being exposed within the shoulder joint. Under such circumstances, it is often necessary or desirable to undergo a partial or total shoulder arthroplasty in order to relieve pain and increase the range of motion of the humerus by rebuilding portions of the shoulder joint.

In performing a total shoulder arthroplasty, a surgeon resects a portion of the proximal end of the humerus that is received by the glenoid fossa, e.g., the humeral head. Once the proximal end of the humerus is resected, the surgeon can then ream the humerus to access the humeral canal. Providing access to the humeral canal allows the surgeon to insert an anchor component, such as a stemmed prosthesis, such as a prosthetic humeral head attached to a stemmed anchor component, into the humeral canal. A hemispheric-shaped prosthetic humeral head can then be attached to a proximal end of the anchor component such that the resected portion of the humerus is replaced by the prosthetic humeral head. If desired, the surgeon can likewise replace a portion of the glenoid fossa with a prosthetic bearing component to provide a bearing surface against which the prosthetic humeral head can be configured to articulate. In a reverse shoulder arthroplasty, the prosthetic humeral head component is attached to the scapula and the prosthetic bearing component is attached to the humerus. Upon completion of the shoulder arthroplasty, pain is typically alleviated, and the patient is provided with an increased range of motion at the shoulder joint.

While conventional shoulder prosthetics used during shoulder arthroplasty adequately provide the patient with an increased range of motion, conventional shoulder prosthetics typically involve insertion of a stem, e.g., a stemmed prosthesis or stemmed anchor, into the humeral canal of the humerus, thereby increasing the overall weight, size, and cost of the humeral component. Furthermore, because the surgeon inserts the stem of the stemmed prosthesis into the humeral canal, the surgical procedure is somewhat complex, as the surgeon first resects the humeral head of the humerus, and subsequently performs one or both of a broaching operation and a reaming operation on the humeral canal prior to inserting the stem of the stemmed prosthesis into the humeral canal. As such, care must be exorcised to not unduly harm the integrity of the humerus and produce additional weaknesses from the removal of bone. Increasing the complexity of the joint-replacement surgery also increases the time in which the surgeon spends in performing the procedure and therefore increases the overall cost of the procedure. Finally, insertion of the stem into the humerus can result in additional bone removal, thereby increasing trauma and post-operative pain.

Examples of humeral broaches are described in Pub. No. US 2020/0315807 to Hatzidakis, titled "Shoulder "Arthroplasty Implant System"; Pub. No. WO/2007/109340 to Reubelt, titled "Femoral and Humeral Stem Geometry and Implantation Method for Orthopedic Joint Reconstruction"; and Pub. No. US 2021/0030552 to Terrill, titled "Keeled Glenoid Implant."

Overview

The present inventors have recognized, among other things, that problems to be solved in preparing a humerus of a shoulder joint to receive a prosthetic component is the difficulty of evaluating and subsequently preparing the humerus for both inlay and onlay anchor components. Inlay and onlay anchor components can be used in stemless humeral implants where bone matter is preserved by avoiding the use of stems. The subject matter of the present application can be applied to both stemmed and stemless humeral prosthetic components, as well as other components that can have different configurations of differing thicknesses. Typical shoulder prostheses include an anchor component, such as the stemmed anchor components discussed above or a stemless anchor component discussed below, that is affixed to a resected bone surface, to which is then attached a prosthetic humeral head component or a prosthetic bearing component for anatomic and reverse shoulder arthroplasties, respectively. However, several factors can affect whether an inlay anchor component or an onlay anchor component is used, such as how much bone is to be removed with the resection to remove diseased or damaged bone, and other factors, such as surgeon preference. Furthermore, the laxity of the shoulder joint, e.g., the tension produced in the joint by ligaments and other soft tissue, is additionally taken into account. With an onlay anchor component, a tray that receives the prosthetic component, e.g., the prosthetic humeral head or prosthetic bearing, lies flush against the resected bone surface. With an inlay anchor component, a tray that receives the prosthetic component, e.g., the prosthetic humeral head or prosthetic bearing, is recessed into the resected bone surface. As such, the humerus is modified differently to prepare the inlay anchor component than the onlay anchor component. Specifically, the resected surface of the humerus is reamed to receive the inlay anchor component. Thus, an onlay anchor component typically occupies more space within the joint than an inlay anchor component. However, due to joint laxity, resection thickness and surgeon preference, it can be difficult to assess ahead of time whether an inlay anchor component or an onlay anchor component will offer the patient the best outcome, e.g., restore the joint to the anatomic tension.

The present subject matter can provide solutions to these and other problems, such as by providing a broaching system that can allow for the assessment of a shoulder joint to determine if an inlay anchor component is desired before reaming of the humerus is performed. A universal broach can be implanted into a resected proximal end of a humerus after performing a resection compatible with both inlay and only anchor components. The universal broach can function as a trial anchor component to assess the laxity of the shoulder joint. In particular, a spacer can be attached to the implanted universal broach to assess joint laxity. The spacer can be engaged with the feature be engaged with the implanted anchor component, such as a prosthetic glenoid attached to the scapula or the anatomic glenoid fossa of the scapula. The spacer can be configured to occupy an equal amount of space within the shoulder joint as a completed inlay anchor component, i.e., an inlay tray and a prosthetic bearing component attached thereto. Thus, if the spacer is loose within the joint, an onlay anchor component can be used since the onlay anchor component is thicker (occupies more space within the joint) than the inlay anchor component. However, if the spacer is tight within the joint or will not fit into the joint, an inlay anchor component can be used since the inlay anchor component is thinner (occupies less space within the joint) than the onlay anchor component. If it is determined that an onlay anchor component is to be used, no further modification of bone is performed. If it is determined that an inlay anchor component is to be used, a reaming guide can be attached to the already-implanted universal broach to guide a reaming operation of the resected surface of the humerus to shape the bone matter above the universal broach to receive the inlay anchor component. As such, a single universal broach can be implanted using a procedure common to both inlay and onlay anchor components.

In an example, a broach for preparing a bone for receiving an anchor for a prosthetic implant can comprise a body comprising a superior surface and a socket extending into the superior surface, and a first anchoring component extending from the body that comprises a spoke extending laterally from the body and a spoke tip extending proximally from the spoke above the superior surface.

In an additional example, a system for preparing a bone for receiving a prosthetic implant can comprise a broach comprising a body comprising a socket extending into a superior surface of the body and an anchoring component extending from the body, a spacer comprising an attachment component configured to attach to the socket and a spacer body attached to the attachment component, an onlay implant comprising a second attachment component configured to attach to the socket, a planar base attached to the second attachment component and a first bearing component attached to the planar base, and an inlay implant comprising a third attachment feature configured to attach to the socket, a bowl-shaped base attached to the third attachment feature and a second bearing component attached to the bowl-shaped base, wherein the spacer body has a thickness that is equal to a maximum gap thickness of the inlay implant.

In another example, a method of implanting a prosthetic component into a bone can comprise inserting a broach into a resected surface of a first bone of a joint, attaching a spacer to the broach, positioning the spacer, while attached to the broach, into a space between the first bone and a second bone of the joint, determining to use an inlay tray or an onlay tray based on laxity of the joint with the spacer inserted therein, attaching the onlay tray to the broach if the joint is loose, and attaching the inlay tray to the broach if the joint is tight.

A system for preparing a bone for receiving an anchor for a prosthetic implant can comprise a first distal broach component comprising a first broach body, a first socket extending into a first superior surface of the first broach body, and a first plurality of cutting spokes extending radially from the first broach body, each of the first plurality of cutting spokes separated by an interval pattern, and a proximal broach component comprising a spacer body configured to attach to the first superior surface of the first broach body, and a plurality of spacer spokes extending radially from the spacer body, each of the plurality of spacer spokes separated by the interval pattern.

A method of implanting a prosthetic component into a bone can comprise resecting surface of a first bone joint, inserting a spacer paddle to assess laxity of the first bone joint, assembling a proximal spacer body with a distal broach body to form a broach assembly, inserting the broach assembly into a resected surface of a first bone of a joint, determining to use an inlay tray or an onlay tray based on the assessed laxity of the first bone joint, attaching the onlay tray to the broach assembly if the joint is loose, and attaching the inlay tray to the distal broach body if the joint is tight.

BRIEF DESCRIPTION OF THE DRAWINGS

FIG. 26A is a side view of a universal broach proximal body and universal broach distal body of a first size.

FIG. 26B is a top view of the universal broach proximal and distal bodies of FIG. 26A inserted into a resected humeral bone.

FIG. 27A is a side view of a universal broach proximal body and a universal broach distal body of a second size.

FIG. 27B is a top view of the universal broach proximal and distal bodies of FIG. 27A inserted into a resected humeral bone.

DETAILED DESCRIPTION

Figure 1:
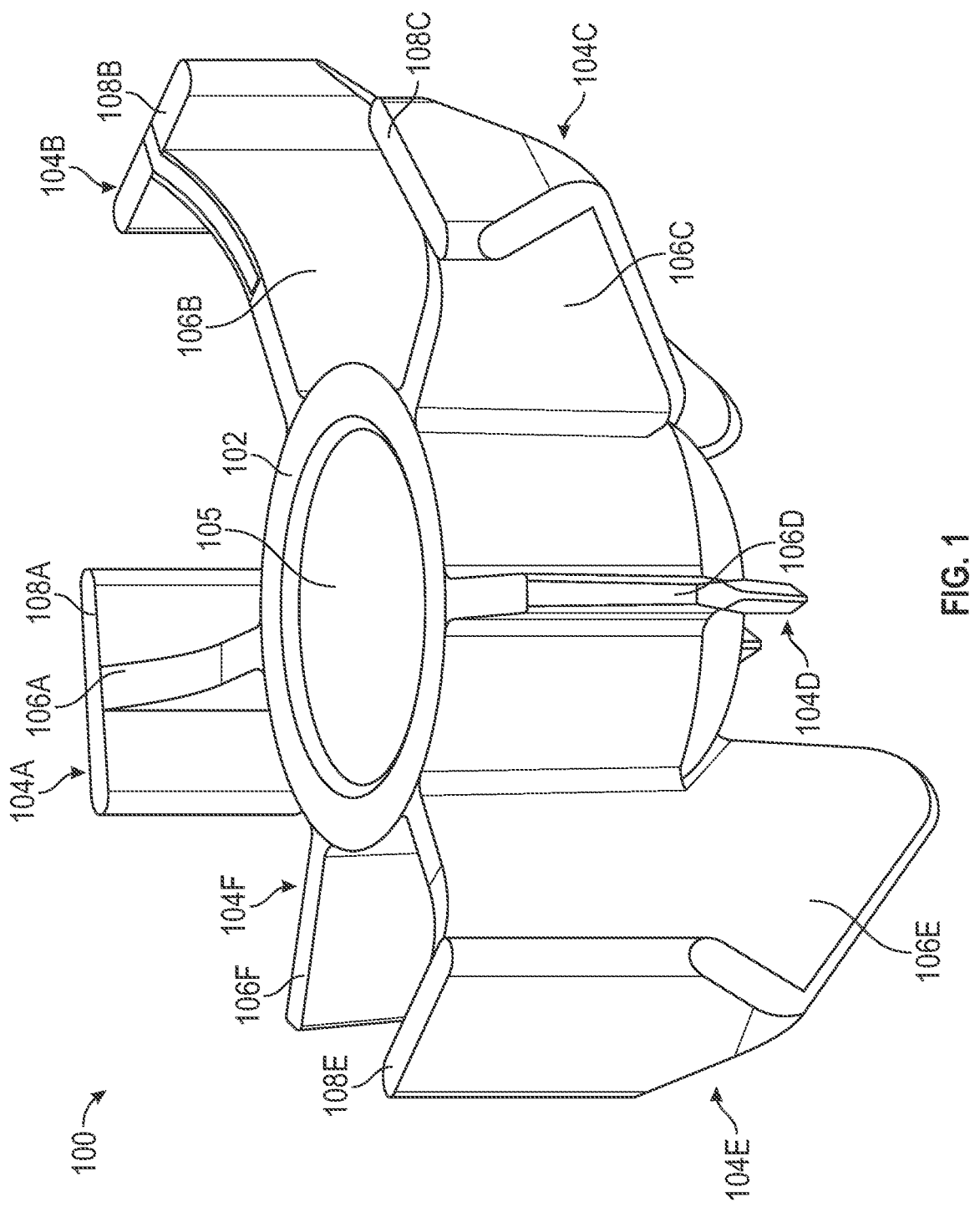
FIG. 1 is a perspective view of a universal broach of the present disclosure configured to broach a humeral bone for inlay and onlay tray configurations.
Figure 2A:
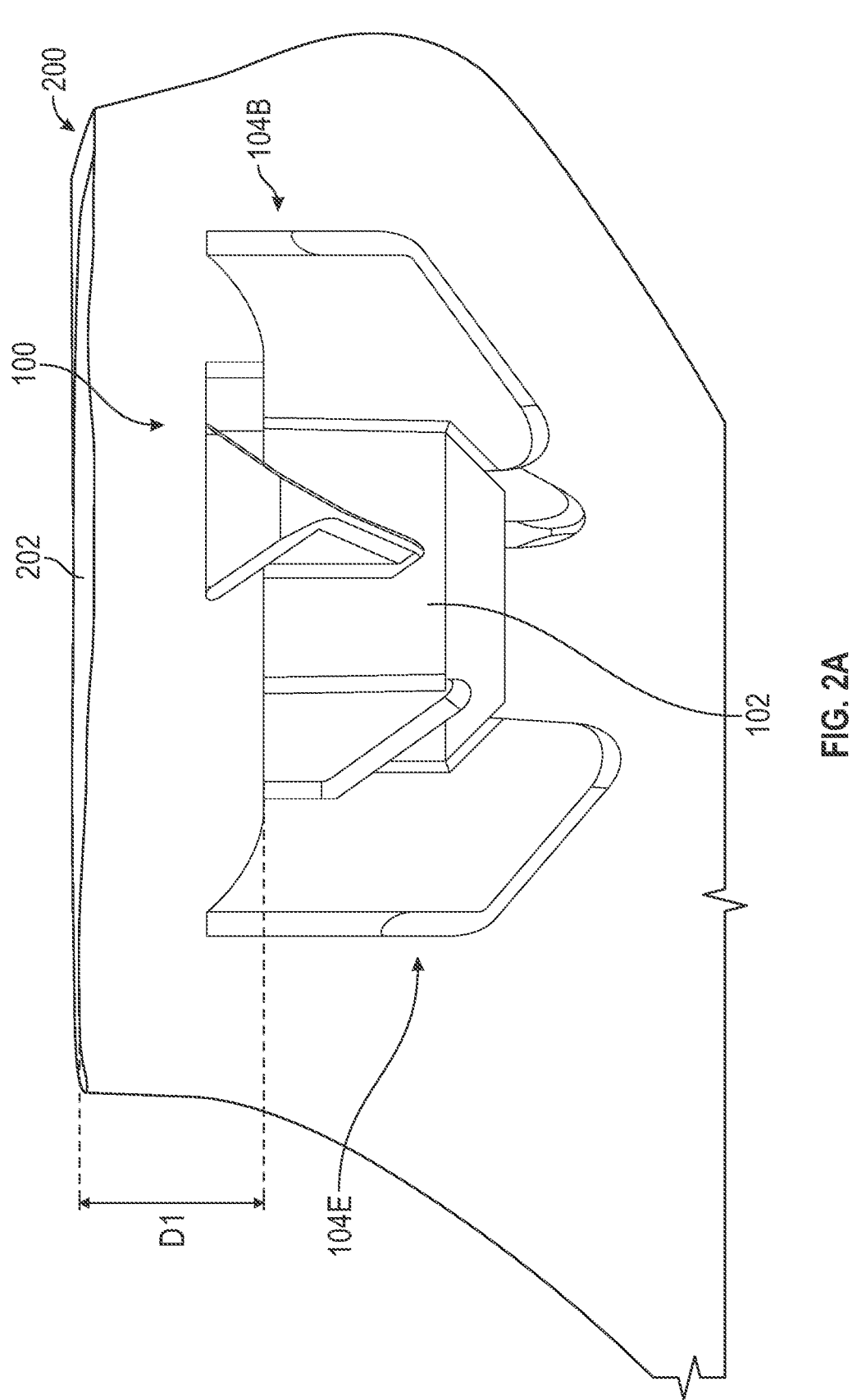
FIG. 2A is a side view of the universal broach of FIG. 1 implanted in a humeral bone for an onlay tray.

FIG. 1 is a perspective view of universal broach 100 of the present disclosure configured to broach a humeral bone, such as humeral bone 200 of FIG. 2A, for inlay and onlay tray configurations. Universal broach 100 can comprise main body 102 and spokes 104A-104F. Main body 102 can comprise socket 105. Spoke 104A can comprise blade 106A and wing 108A. Spoke 104B can comprise blade 106B and wing 108B. Spoke 104C can comprise blade 106C and wing 108C. Spoke 104D can comprise blade 106D. Spoke 104E can comprise blade 106E and wing 108E. Spoke 104F can comprise blade 106F.

Universal broach 100 can be configured to be inserted into bone so that spokes 104A-104F can function to cut the bone to form envelope 140 (FIG. 3A) or template that can receive an implantable anchor component after universal broach 100 is removed. Main body 102 and spokes 104A-104F can have the same or similar shape as the anchor component, which is shaped to be implanted into bone to provide a secure attachment to the bone matter, e.g. a tight fit that prevents rotation and dislodgment. Thereafter a prosthetic component, e.g., a prosthetic humeral head component or a prosthetic bearing component, can be attached to the implantable anchor component. Different configurations of the prosthetic components can be attached to the same anchor component. Universal broach 100 can be shaped to provide insertion of a single anchor component that can accommodate different shaped prosthetic components. In particular, two different types of trays, an inlay tray and an onlay tray, can be used with the anchor component to hold various prosthetic bearing components of different thicknesses. Universal broach 100 can be attached to onlay tray 206 and prosthetic bearing component 230 of FIGS. 2A and 2B and inlay tray 250 and prosthetic bearing component 270 of FIGS. 3A and 3B.

Universal broach 100 can be used to couple to trial trays so that a surgeon can determine if an inlay tray or an onlay tray is needed or desired before constructing the final implantable device. Inserter 300 (FIGS. 4A-5B) can be used to insert universal broach 100 into a bone. Spacer 400 (FIGS. 6A-6C) can be attached to universal broach 100 to assist a surgeon in determining if an inlay tray or an onlay tray will be used. Reaming guide 500 (FIG. 7) can be attached to universal broach 100 to allow reamer 520 (FIG. 9) to ream the bone (e.g., humeral bone 200 of FIG. 2A) to receive an inlay tray. As such, universal broach 100 can be used to implant humeral head or bearing components in both inlay and onlay configurations and only one broaching operation can be performed, with universal broach 100 remaining in place until the final prosthetic construct is determined and prepared for implantation. Thus, multiple broaching operations or multiple steps of inserting various components into the bone to decide the final prosthetic construct can be avoided.

Figure 2B:
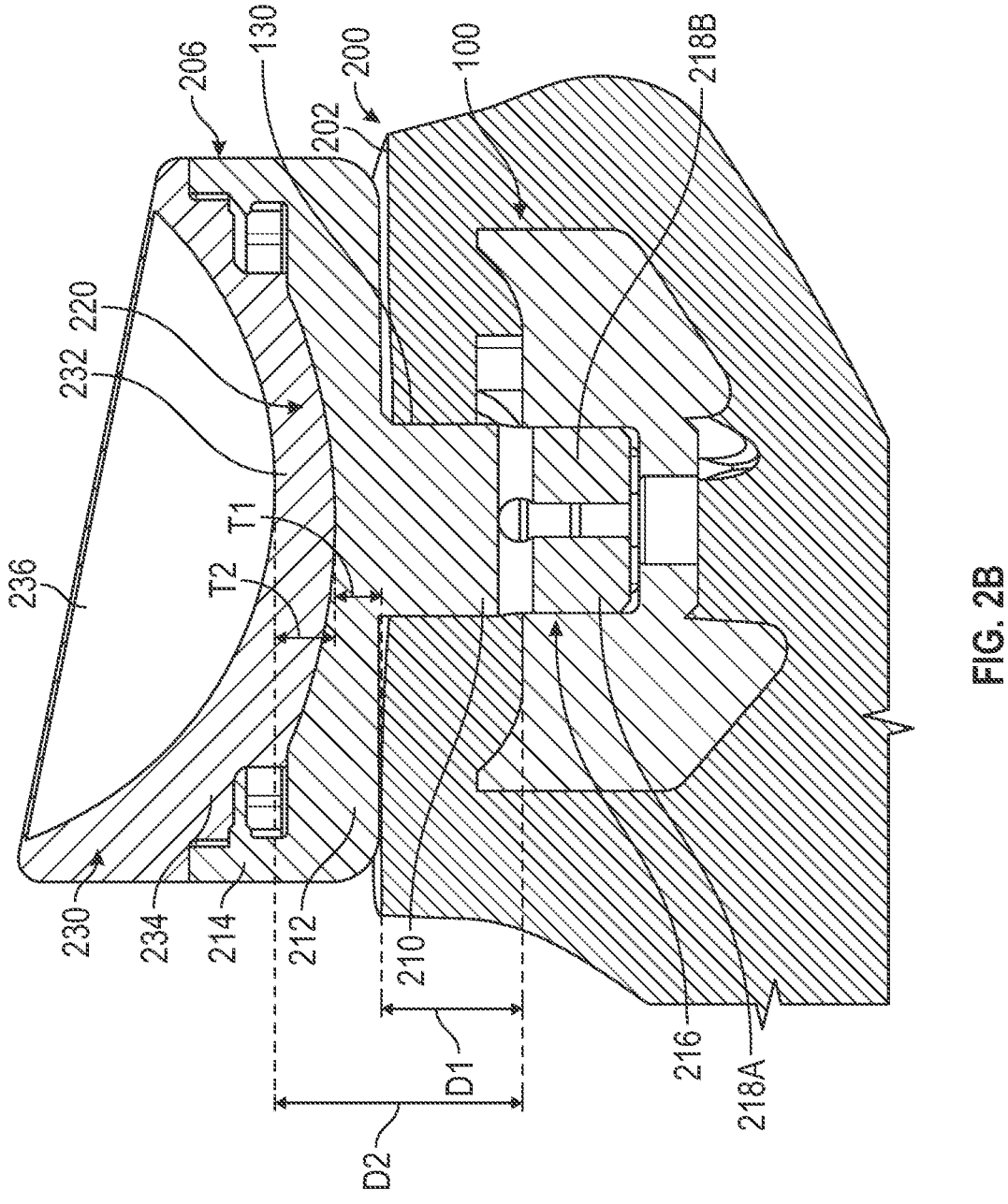
FIG. 2B is a cross-sectional view of the universal broach of FIG. 2A with an onlay tray and bearing component attached thereto.

FIG. 2A is a side view of universal broach 100 of FIG. 1 implanted in humeral bone 200 for onlay tray 206 of FIG. 2B. FIG. 2B is a cross-sectional view of universal broach 100 of FIG. 2A with onlay tray 206 attached thereto. FIGS. 2A and 2B are discussed concurrently.

Humeral bone 200 can include resected surface 202. Onlay tray 206 can comprise stem 210, base 212 and wall 214. Stem 210 can comprise attachment portion 216 that comprises arms 218A and 218B. Base 212 and wall 214 can form socket 220. Onlay tray 206 can be attached to prosthetic bearing component 230. Prosthetic bearing component 230 can comprise base 232, attachment portion 234 and cup 236.

In an onlay procedure, onlay tray 206 is attached to universal broach 100 so that base 212 lies flush against resected surface 202. As such, onlay tray 206 lies outside of, or on top of, humeral bone 200.

Universal broach 100 can be implanted into humeral bone 200 distance D1 below resected surface 202. Specifically, the tops or proximal-most side of blades 106A-106F can be located below resected surface 202 distance D1. Thereafter, attachment portion 216 of stem 210 can be inserted into socket 105 of universal broach 100. Attachment portion 216 can provide a means for maintaining onlay tray 206 engaged with universal broach 100. Arms 218A and 218B can flex to engage with socket 105 to maintain a tight fit. However, arms 218A-218B can be deflected, such as by tipping onlay tray 206, to facilitate removal of onlay tray 206 from universal broach 100.

Thus, prosthetic bearing component 230 can be located above universal broach 100 and resected surface 202. More specifically, the bottom of cup 236 can be located distance D2 above the tops of spokes 104A-104F. Distance D2 can be determined by thickness T1 of base 212 of onlay tray 206 and thickness T2 of base 232 of prosthetic bearing component 230. In examples, onlay tray 206 and prosthetic bearing component 230 can come in different sizes where thicknesses T1 and T2 can be different. That is, thickness T1 can come in two different thicknesses and thickness T2 can come in two different thicknesses. As such, distance D2 can have four different lengths. In each configuration, base 232 of onlay tray 206 and all of prosthetic bearing component 230 can be located above resected surface 202.

Figure 3A:
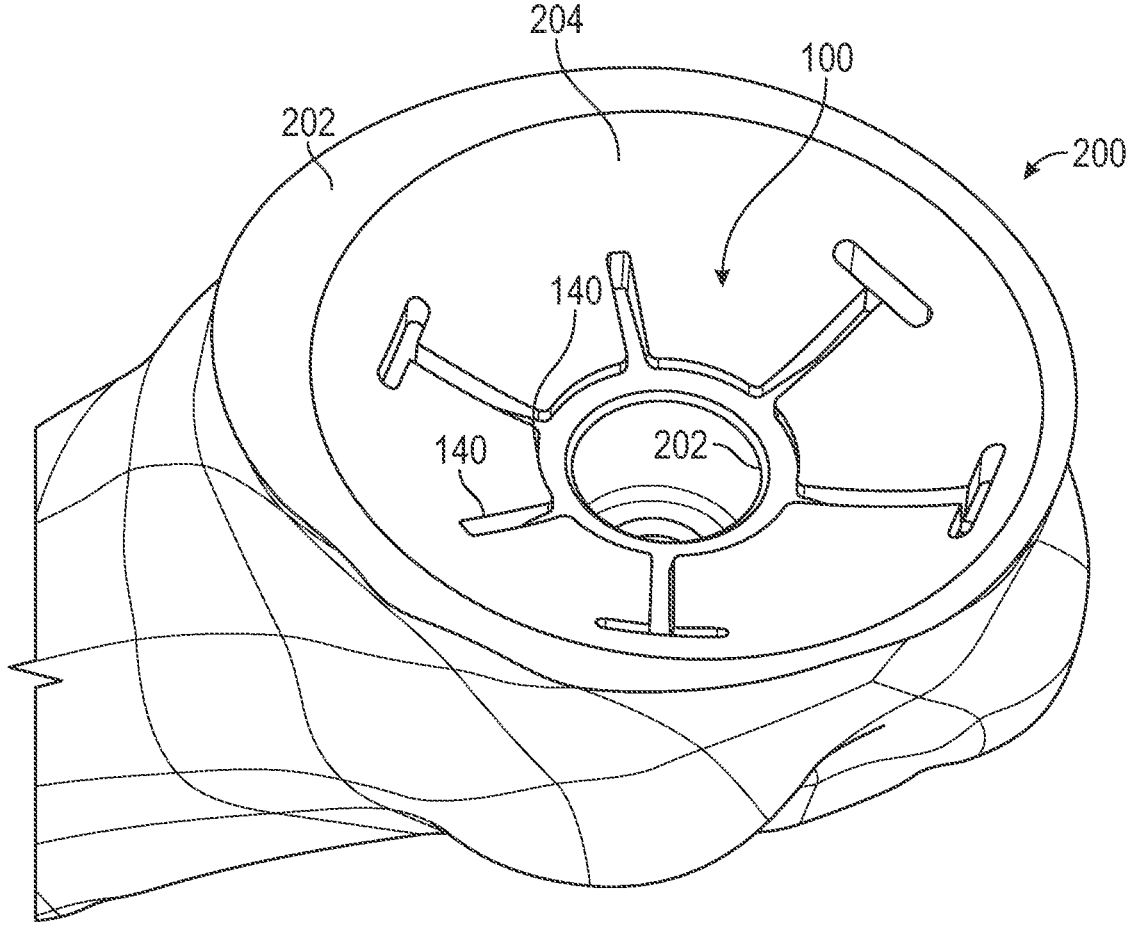
FIG. 3A is a side view of the universal broach of FIG. 1 implanted in a humeral bone for an inlay tray.
Figure 3B:
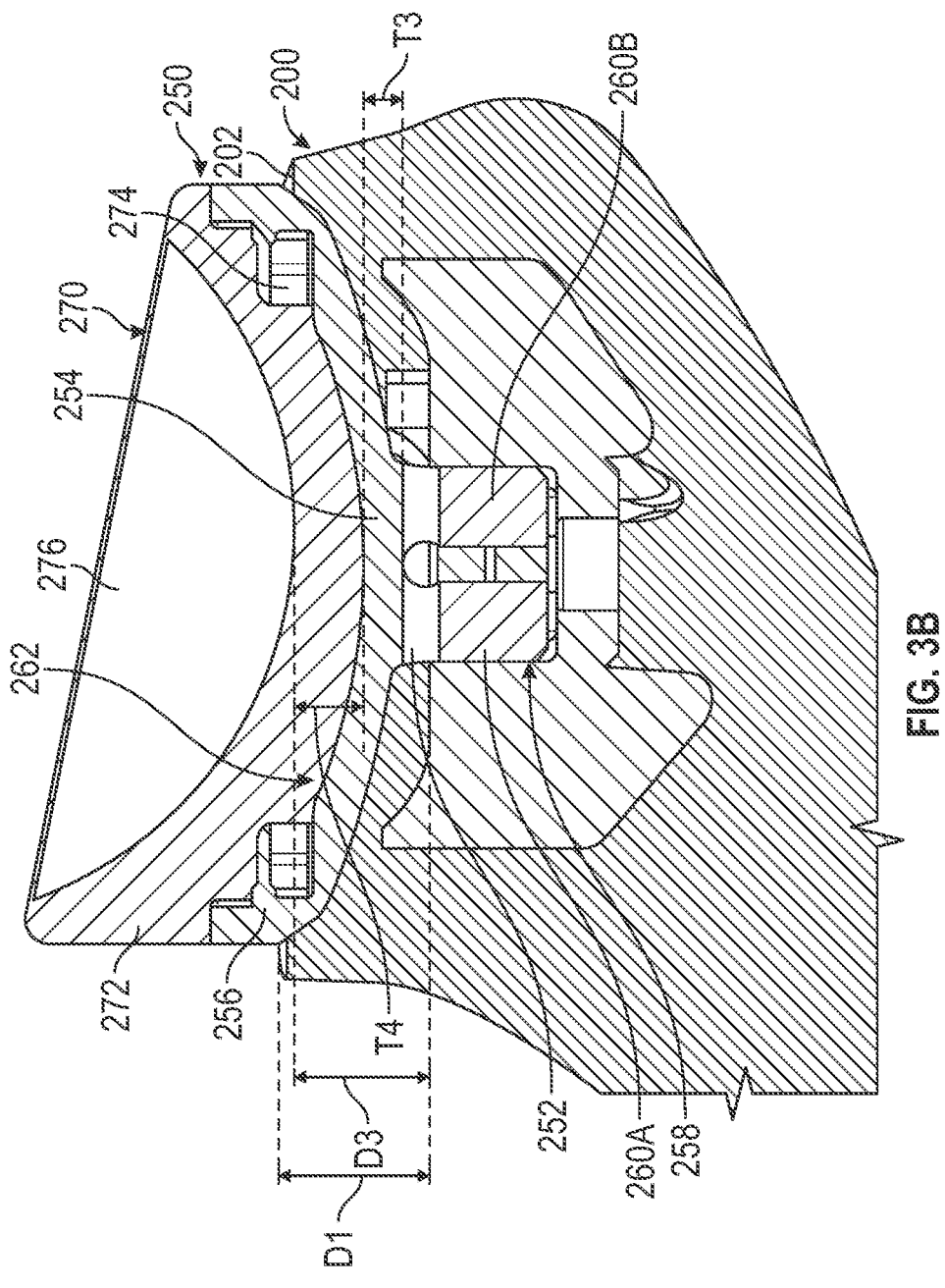
FIG. 3B is a cross-sectional view of the universal broach of FIG. 3A with an inlay tray and bearing component attached thereto.

FIG. 3A is a side view of universal broach 100 of FIG. 1 implanted in humeral bone 200 for inlay tray 250 of FIG. 3B. FIG. 3B is a cross-sectional view of universal broach 100 of FIG. 3A with inlay tray 250 attached thereto. FIGS. 3A And 3B are discussed concurrently.

Humeral bone 200 can comprise resected surface 202 and reamed depression 204. Inlay tray 250 can comprise stem 252, base 254 and wall 256. Stem 252 can comprise attachment portion 258 that comprises arms 260A and 260B. Base 254 and wall 256 can form socket 262. Inlay tray 250 can be coupled to prosthetic bearing component 270. Prosthetic bearing component 270 can comprise base 272, attachment portion 274 and cup 276.

In an inlay procedure, inlay tray 250 is attached to universal broach 100 so that base 254 is recessed into resected surface 202. As such, inlay tray 250 lies inside of, or within, humeral bone 200 within depression 204. Depression 204 can be formed with reamer 520 of FIGS. 9A-10B.

Universal broach 100 can be implanted into humeral bone 200 distance D1 below resected surface 202. Specifically, the tops or proximal-most side of blades 106A-106F can be located below resected surface 202 distance D1. Thereafter, attachment portion 258 of stem 252 can be inserted into socket 105 of universal broach 100. Attachment portion 258 can provide a means for maintaining inlay tray 250 engaged with universal broach 100. Arms 260A and 260B can flex to engage with socket 105 to maintain a tight fit. However, arms 260A-260B can be deflected, such as by tipping inlay tray 250, to facilitate removal of inlay tray 250 from universal broach 100.

Thus, prosthetic bearing component 270 can be located above universal broach 100. More specifically, the bottom of cup 276 can be located distance D3 above the tops of spokes 104A-104F. Distance D3 can be determined by thickness T3 of base 254 of inlay tray 250 and thickness T4 of base 272 of prosthetic bearing component 270. In examples, inlay tray 250 and prosthetic bearing component 270 can come in different sizes where thicknesses T3 and T4 can be different. That is, thickness T3 can come in two different thicknesses and thickness T4 can come in two different thicknesses. As such, distance D4 can have four different lengths. In each configuration, base 254 of inlay tray 250 can be recessed within resected surface 202, but the bottom of cup 276 can be located above or below resected surface 202 depending on the selected thicknesses for T3 and T4.

In examples, prosthetic bearing component 270 and prosthetic bearing component 230 can be interchangeable such that the universal broaching system of the present application can be supplied with fewer components. In examples, thickness T3 can be X mm thick or X+5 mm thick. In examples, thickness T1 can be Y mm thick or and X+5 mm thick. In examples, thickness T2 and thickness T4 can be Z mm thick and Z+3 mm thick. In examples, a combination of X+Z can place cup 276 one and a half mm below resected surface 202 in a minimum configuration. Thus, the bottom of cup 276 can be placed six and a half mm above resected surface 202 in a maximum configuration. In examples, a combination of Y+Z can place cup 236 four and a half mm above resected surface 202. Thus, the bottom of cup 236 can be placed twelve and a half mm above resected surface 202 in a maximum configuration.

As can be seen in FIGS. 2B and 3B, universal broach 100 is implanted the same depth D1 for onlay tray 206 and inlay tray 250. Thus, universal broach 100 can be inserted using the same procedure for both onlay tray 206 and inlay tray 250. However, onlay tray 206 and inlay tray 250 are implanted with humeral bone 200 modified in different ways. In particular, inlay tray 250 involves reaming resected surface 202 so that inlay tray 250 can be recessed into humeral bone 200. However, it is not always clear to a surgeon due to, for example, the soft tissue, e.g., ligaments, condition, if onlay tray 206 or inlay tray 250 will offer the patent a better patient outcome, e.g., an anatomically tensioned joint, until after the joint is trialed. Universal broach 100 allows the joint laxity or tightness to be evaluated before reaming of humeral bone 200 so that it can be determined if onlay tray 206 will provide sufficient tensioning of the joint without reaming or if inlay tray 250 can be used with the additional step of reaming bone 202 to form reamed depression 204. In particular, universal broach 100 can be inserted into resected surface 202 and then attached to spacer 400 to evaluate the laxity of the shoulder joint.

Figure 4B:
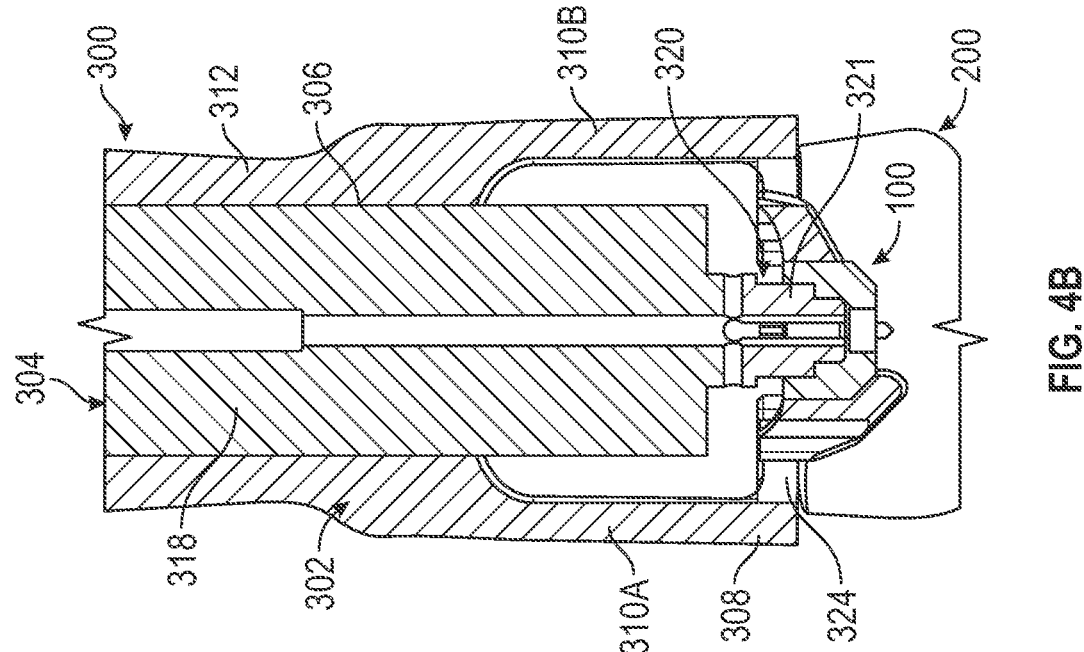
FIG. 4B is a cross-sectional view of the inserter and universal broach of FIG. 4A.
Figure 4A:
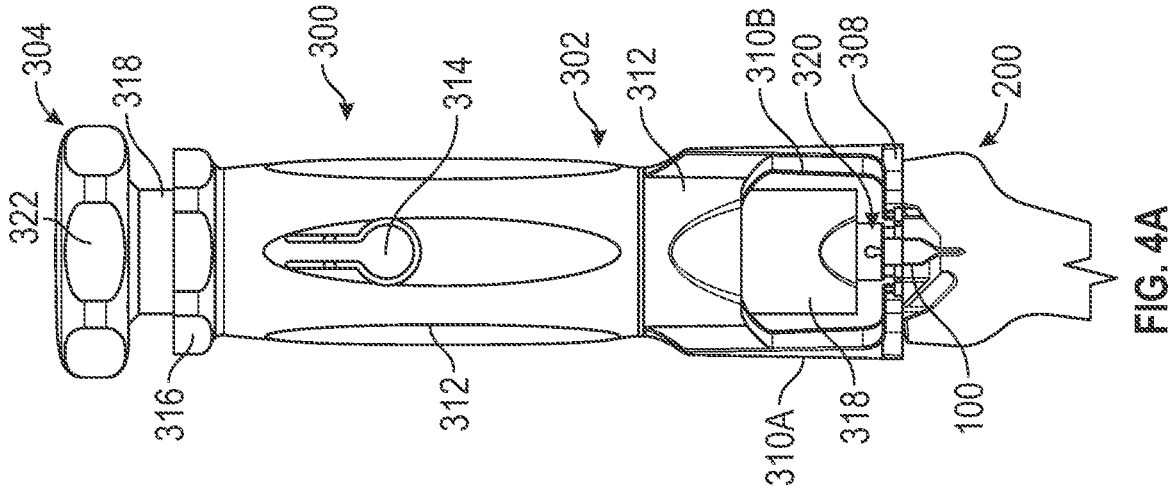
FIG. 4A is a side view of the universal broach of FIG. 1 attached to an inserter in a retracted state for insertion into bone.
Figure 5B:
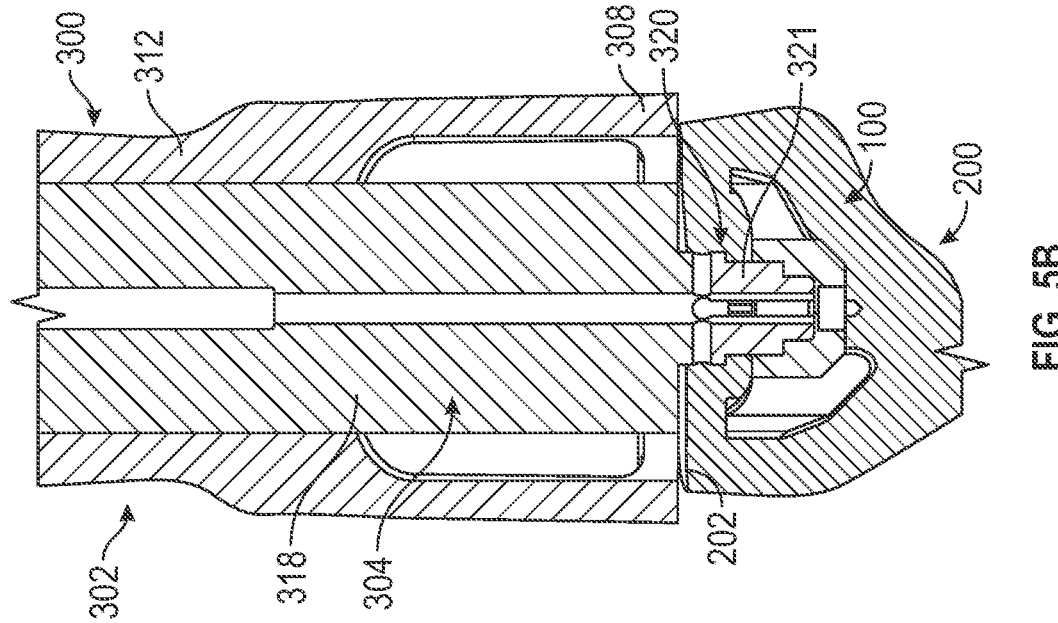
FIG. 5B is a cross-sectional view of the inserter and universal broach of FIG. 5A.
Figure 5A:
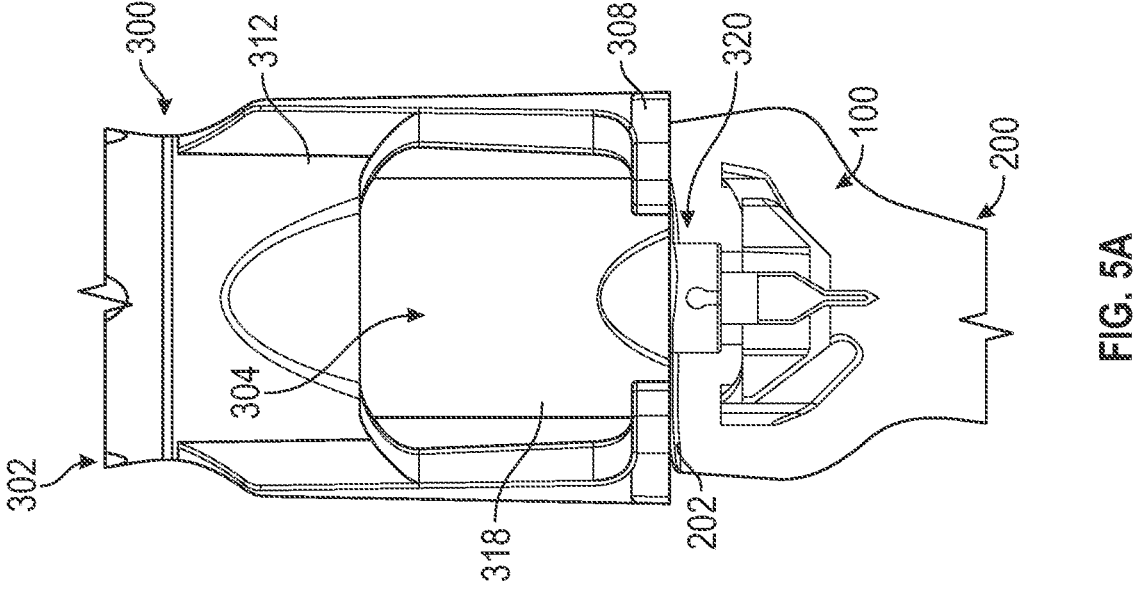
FIG. 5A is a side view of the universal broach and the inserter of FIG. 4A in an extended state to push the universal broach further into bone.

FIG. 4A is a side view of inserter 300 attached to universal broach 100 of FIG. 1 in a retracted state. FIG. 4B is a cross-sectional view of inserter 300 and universal broach 100 of FIG. 4A. FIG. 5A is a side view of inserter 300 of FIG. 4A in an extended state to push universal broach 100 into humeral bone 200. FIG. 5B is a cross-sectional view of inserter 300 and universal broach 100 of FIG. 5A. FIGS. 4A-5B are discussed concurrently.

Inserter 300 can comprise base 302 and handle 304. Handle 304 can be slidable within channel 306 of base 302 to push universal broach 100 into bone matter. Base 302 can comprise channel 306, plate 308, arms 310A and 310B, shaft 312, lock 314 and knob 316. Handle 304 can comprise shaft 318, attachment portion 320 and knob 322.

Humeral bone 200 can be resected to remove the humeral head and to form resected surface 202. A surgeon can measure the cross-sectional area or diameter of resected surface 202 to determine an appropriate size, e.g., small, medium or large, of prosthetic components to be implanted in humeral bone 200. A sizer can be used to place a pin at the center or central portion of resected surface 202.

A pin can be placed in the center of resected surface 202. Then a reamer can be used to remove a small cylindrical shaped portion of bone matter surrounding the pin to facilitate insertion of universal broach 100. In examples, the diameter of the reamer can correspond to the diameter of main body 102 of universal broach 100. For example, FIGS. 2B and 6C show channel 130 formed in humeral bone 200 surrounding stem 210.

Universal broach 100 can be loaded into inserter 300 by inserting attachment portion 320 into socket 105 of main body 102 on universal broach 100. Attachment portion 320 can be spaced from the bottom surface of shaft 318 by extension 321. Plate 308 can include opening 324 into which universal broach 100 can be inserted to connect to attachment portion 320. Lock 314 can be used to immobilize shaft 318 of handle 304 within channel 306 of shaft 312 of base 302. In examples, shaft 318 can be spring-loaded within channel 306 and lock 314 can immobilize shaft 318 with an actuating spring in a compressed state. In the locked position, blades 106A-106F of universal broach 100 can protrude beyond plate 308. A surgeon can manually align blades 106A-106F within the boundary of resected surface 202, such as at channel 130. A surgeon can then push blades 106A-106F into bone matter below resected surface 202 until plate 308 contacts resected surface 202, as shown in FIGS. 4A and 4B. Lock 314 can be released to allow shaft 318 to be slidable within channel 306. A surgeon can grasp handle 304 with one hand and push down on knob 322 to advance shaft 318 along channel 306 to extend attachment portion 320 beyond plate 308 to move universal broach 100 outside of channel 306 and further into the bone matter below resected surface 202, as shown in FIGS. 5A and 5B. In examples, lock 314 can release compression of an actuation spring such that shaft 318 of handle 304 can be self-actuated to push universal broach into bone matter. Shaft 318 can be advanced so that the bottom of shaft 318 can be flush with the bottom of plate 308 against resected surface 202, with attachment portion 320 extending into bone matter. Thereafter, inserter 300 can be removed from universal broach 100 by removing attachment portion 320 from socket 105. As such, universal broach 100 can be left in humeral bone 200 as shown in FIG. 2A, with the tops of blades 106A-106F distance D1 below resected surface. Inserter 300 can be used to insert universal broach 100 a fixed distance below resected surface 202 a predetermined amount that can correlate to the amount that attachment portion 216 of onlay tray 206 and attachment portion 258 of inlay tray 250 are configured to extend into bone. Inserter 300 provides a repeatable insertion process that can reproduce a length for distance D1 that is repeatable every time shaft 318 is actuated as described above.

Figure 6A:
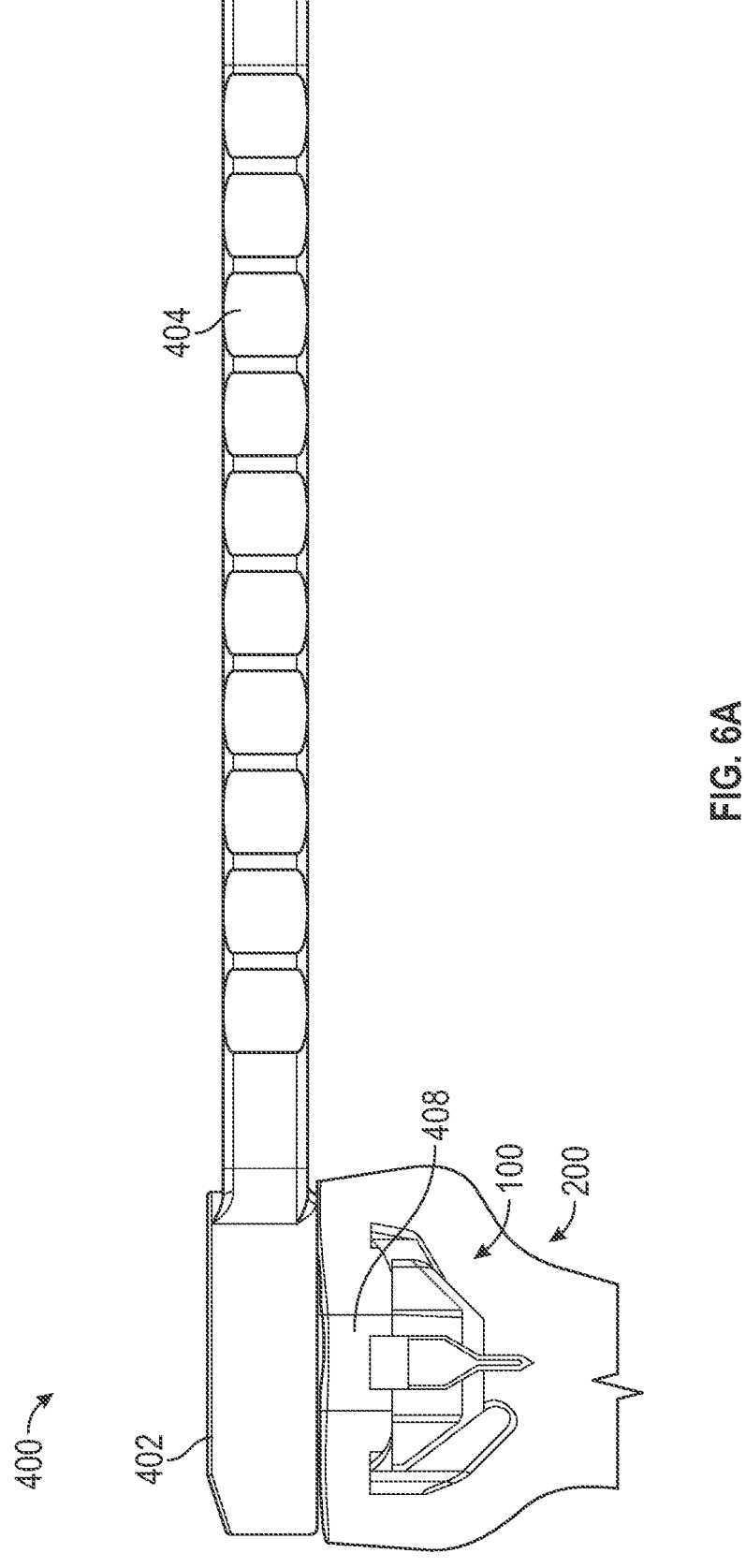
FIG. 6A is a side view of the universal broach of FIG. 1 inserted into a humeral bone while attached to a spacer.
Figure 6B:
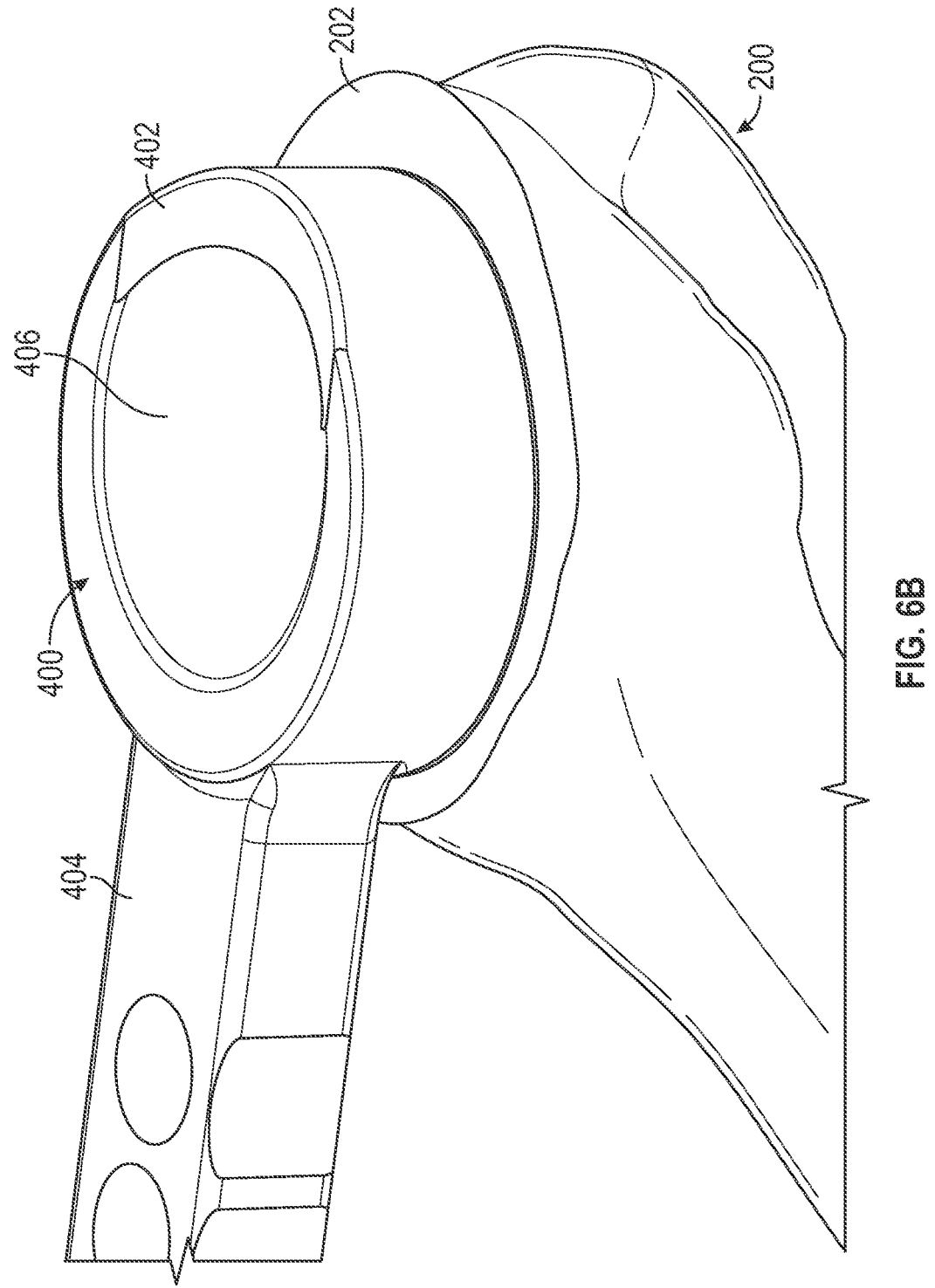
FIG. 6B is a top perspective view of the spacer of FIG. 6A showing an articulating surface for engaging a prosthetic head implant.
Figure 6C:
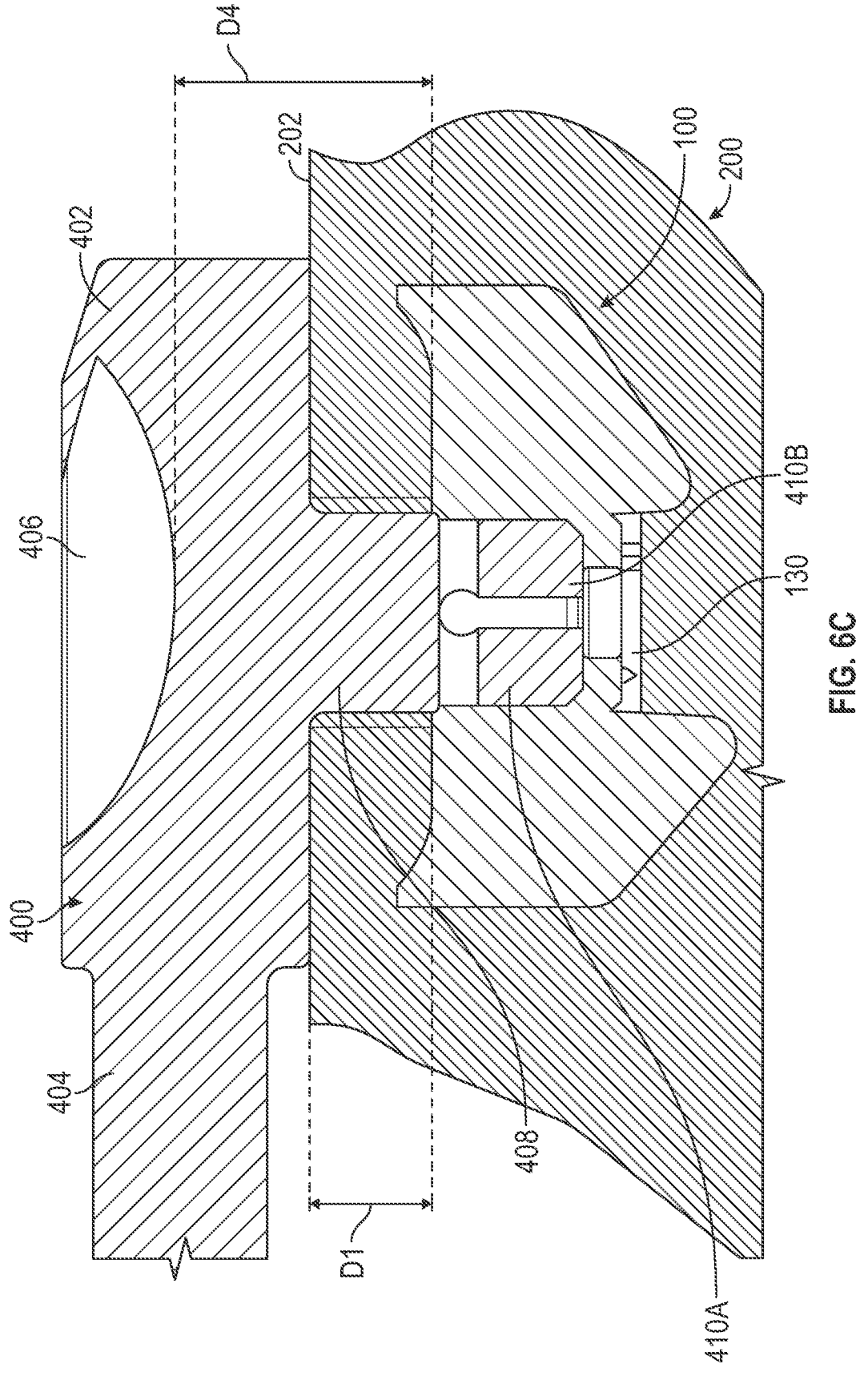
FIG. 6C is a side cross-sectional view of the space of FIG. 6A showing an attachment portion for the universal broach.

FIG. 6A is a side view of spacer 400 attached to universal broach 100 that is inserted into humeral bone 200. Spacer 400 can comprise head 402 and handle 404. FIG. 6B is a top perspective view of spacer 400 of FIG. 6A showing articulating surface 406 for engaging a prosthetic head implant. FIG. 6C is a side cross-sectional view of spacer 400 of FIG. 6A showing attachment portion 408 for universal broach 100. FIGS. 6A-6C are discussed concurrently.

After universal broach 100 has been implanted into humeral bone 200 using inserter 300, spacer 400 can be attached to universal broach 100. Attachment portion 408 can be inserted into socket 105 of universal broach 100. As can be seen in FIG. 6C, attachment portion 408 can comprise arms 410A and 410B. Attachment portion 408 can provide a means for maintaining spacer 400 engaged with universal broach 100. Arms 410A and 410B can flex to engage with socket 105 to maintain a tight fit. However, arms 410A-410B can be deflected, such as by tipping spacer 400, to facilitate removal of spacer 400 from universal broach 100. Handle 404 can be attached to head 402 to facilitate movement of spacer 400 within a joint such that spacer 400 can comprise a spacer paddle.

Figure 13:
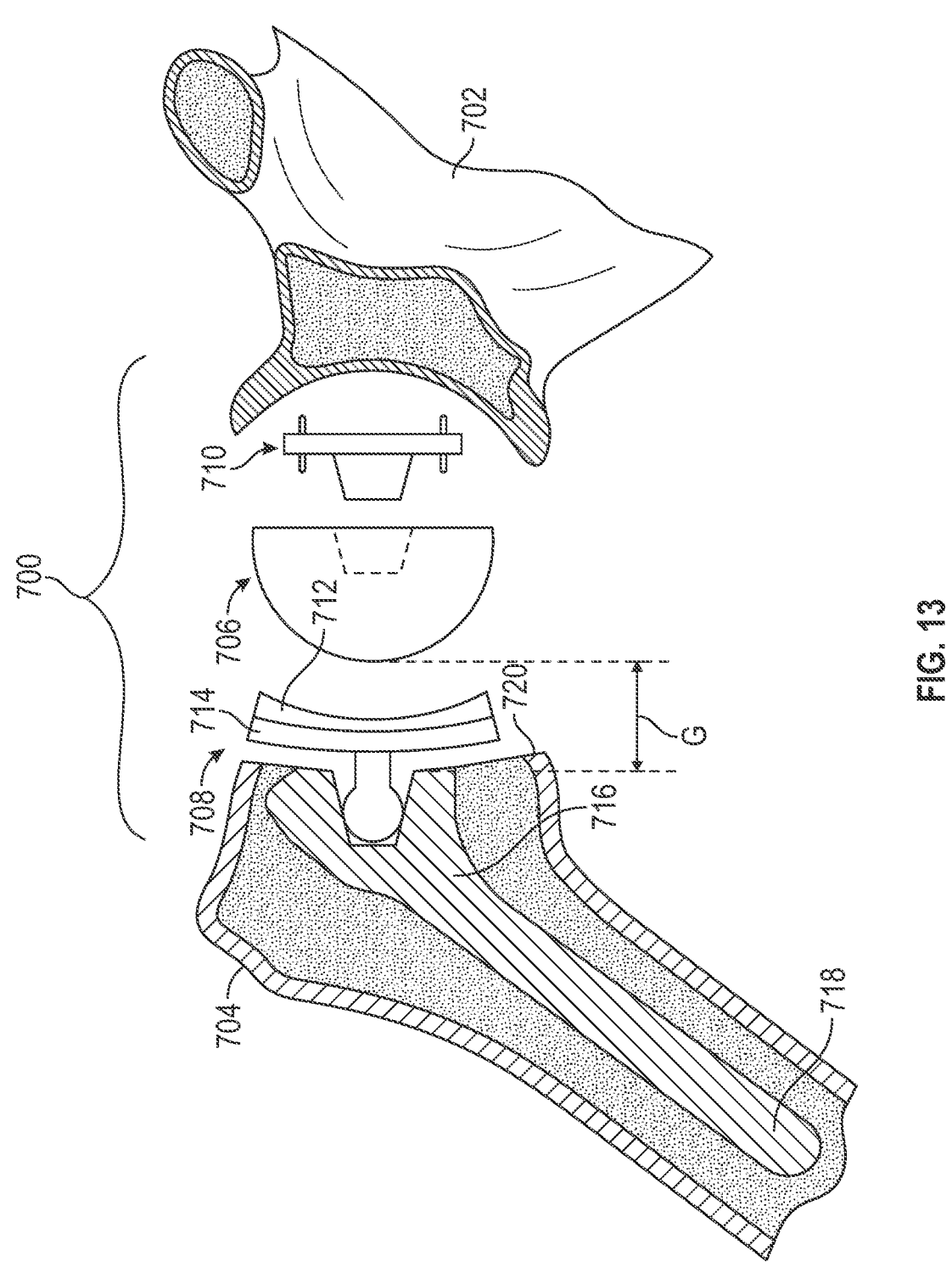
FIG. 13 is a schematic view of a shoulder joint configured to receive a total shoulder joint replacement in a reverse shoulder configuration, in an example of the present disclosure.

Universal broach 100 can be used to evaluate ligament tension, e.g., laxity, within a joint, e.g., shoulder joint 700 of FIG. 13. For example, universal broach 100 while inserted into humeral bone 200 and attached to spacer 400 can be positioned adjacent a scapula. For illustration, universal broach 100 can be implanted into humerus 704 (FIG. 13) and spacer 400 can be positioned against prosthetic glenoid 706 implanted into scapula 702. Thereafter, soft tissue such as ligaments can pull humerus 704 toward scapula 702 such that spacer 400 is brought into engagement with prosthetic glenoid 706 if the soft tissue permits spacer 400 to be fit within the space, e.g., gap G of FIG. 13.

Spacer 400 can be designed to provide the maximum offset provided by inlay tray 250 plus prosthetic bearing component 270. The maximum offset provided by inlay tray 250 and prosthetic bearing component 270 can be provided by using a combination of an inlay tray 250 configured to have the maximum thickness of thickness T3 and prosthetic bearing component 270 configured to have the maximum thickness of thickness T4. The combination of the maximum amounts of thickness T3 and thickness T4 can result in distance D3 being equal to distance D4 of spacer 400. Distance D4 can be measured from the bottom of articulating surface 406 to the tops of spokes 104A-104F when universal broach 100 is attached to spacer 400. Thus, distance D4 can be configured to be equal to distance D3 for the combination of maximum thickness of T3 and T4. Distance D2 minus distance D1 can be considered a gap height provided by onlay tray 206 and prosthetic bearing component 230. Distance D3 minus distance D1 can be considered a gap height provided by inlay tray 250 and prosthetic bearing component 270. Thus, if spacer 400 is loose within the joint, that is an indication that it is desirable to use onlay tray 206 and prosthetic bearing component 230, which provides a greater amount of offset compared to inlay tray 250 and prosthetic bearing component 270. Spacer 400 being loose within the joint can mean that no combination of inlay tray 250 and prosthetic bearing component 270 can be assembled to take the slack out of the joint. Thus, combinations of onlay tray 206 and prosthetic bearing component 230 that can have combinations of thicknesses T1 and T2 that are greater than distance D4 minus D1 can be used to fill the joint. However, if spacer 400 is tight within the joint, or will not fit into the joint, that is an indication that it is desirable to use inlay tray 250, after resected surface 202 is reamed to remove additional bone matter (if needed depending on the combination of inlay thicknesses T3 and T4. Combinations of inlay tray 250 and prosthetic bearing component 270 can be made to have thicknesses T3 and T4 that are smaller than distance D4 minus D1 that will fit in the joint.

After the laxity of the joint is determined using spacer 400, spacer 400 can be removed from universal broach 100 and universal broach 100 can be left in the joint. Universal broach 100 can allow trialing of the joint using inlay or onlay implant trials, such as those shown in FIGS. 2A-3B, whichever is decided. If it is determined to use onlay tray 206, resected surface 202 can be left alone. However, if it is determined to use inlay tray 250, resected surface 202 can be reamed using reamer 520.

Figure 7:
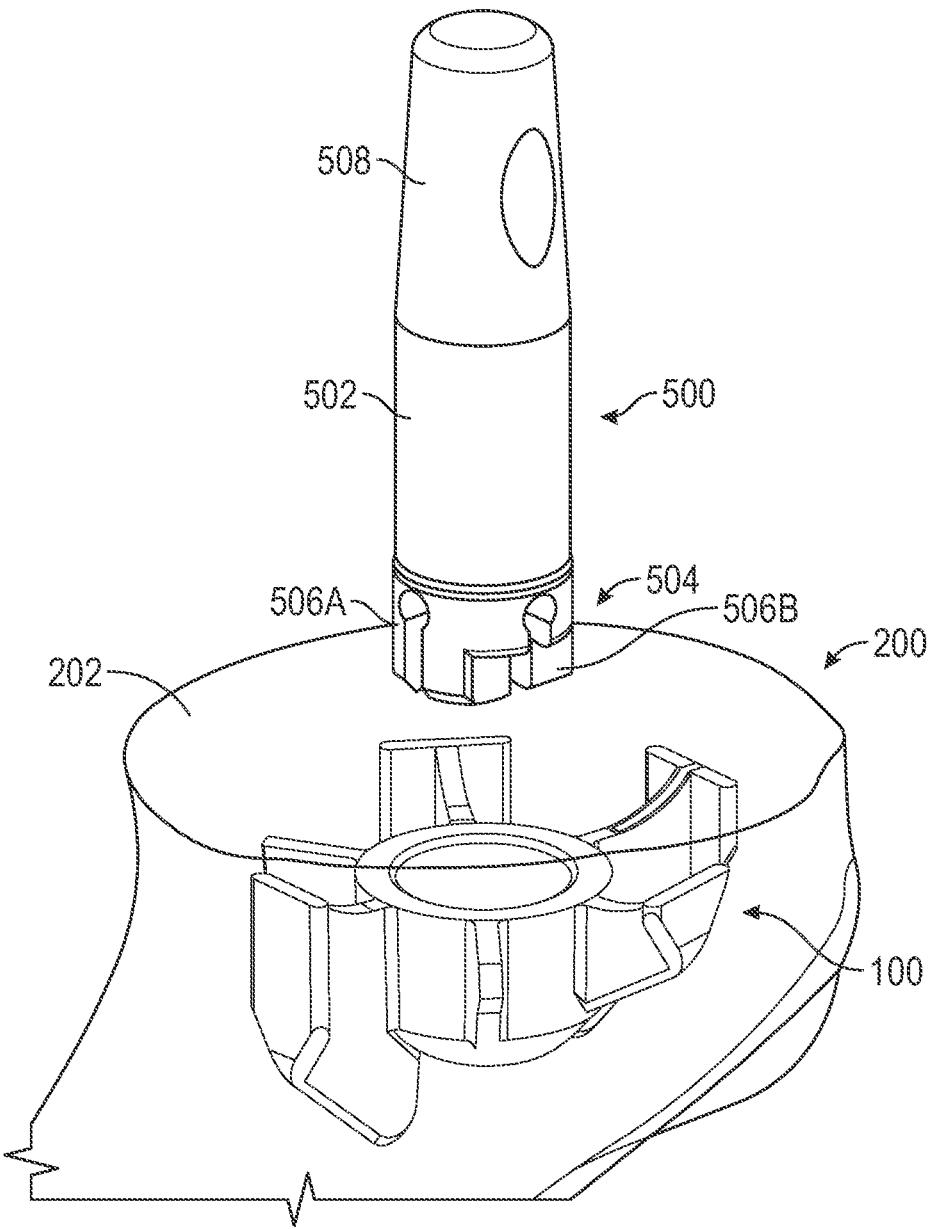
FIG. 7 is a perspective view of the universal broach of FIG. 1 inserted into bone with a reaming guide exploded therefrom.
Figures 8A, 8B:
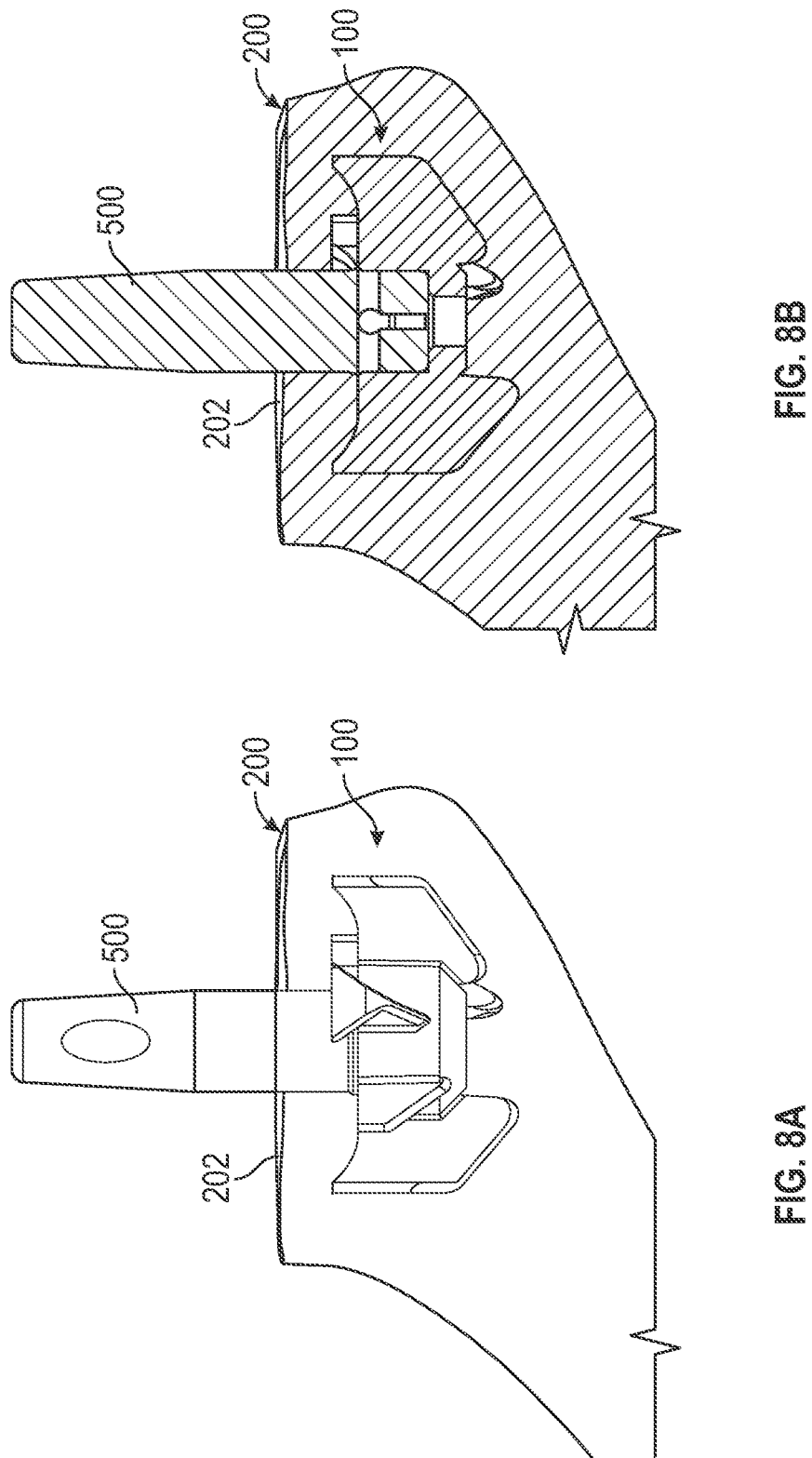
FIG. 8A is a side view of the reaming guide attached to the universal broach of FIG. 7.
FIG. 8B is a cross-sectional view of the reaming guide and universal broach of FIG. 8A.

FIG. 7 is a perspective view of universal broach 100 of FIG. 1 inserted into humeral bone 200 with reaming guide 500 exploded therefrom. Reaming guide 500 can comprise shaft 502 and attachment portion 504. Attachment portion 504 can comprise arms 506A and 506B. Shaft 502 can comprise tapered tip 508. FIG. 8A is a side view of reaming guide 500 attached to universal broach 100 of FIG. 7. FIG. 8B is a cross-sectional view of reaming guide 500 and universal broach 100 of FIG. 8A. FIGS. 7-8B are discussed concurrently.

Reaming guide 500 can provide a rail or peg over which a reaming device, such as reamer 520, can be positioned and slid up and down. Tapered tip 508 can comprise a narrowed section compared to shaft 502 that can facilitate insertion of reaming guide 500 into socket 530 of reamer 520, such as socket 530 of FIG. 10A. The diameter of shaft 502 between tapered tip 508 and attachment portion 504 can be slightly smaller than socket 530 to maintain reamer 520 centered on reaming guide 500. Attachment portion 504 can provide a means for maintaining reaming guide 500 engaged with universal broach 100. Arms 506A and 506B can flex to engage with socket 105 to maintain a tight fit. However, arms 506A-506B can be deflected, such as by tipping reaming guide 500, to facilitate removal of reaming guide 500 from universal broach 100.

Figure 9:
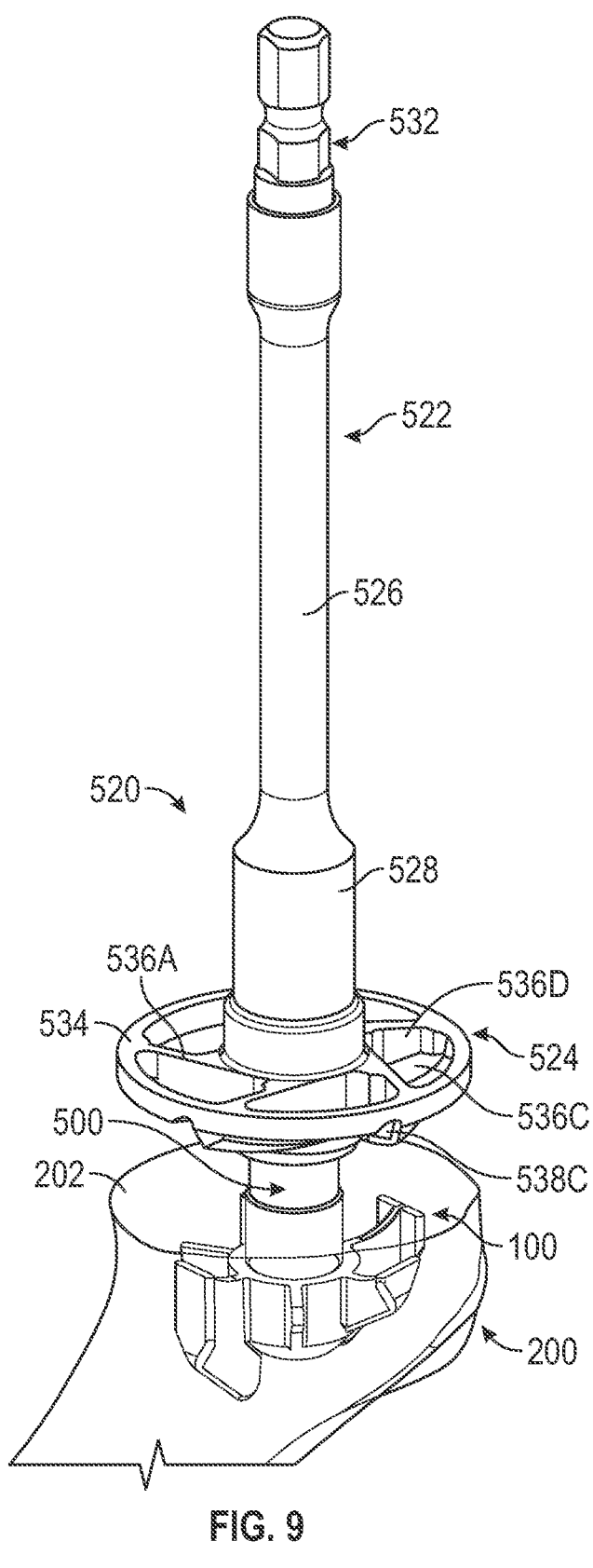
FIG. 9 is a perspective view of a reamer disposed over the reaming guide of FIGS. 8A and 8B.

FIG. 9 is a perspective view of reamer 520 disposed over reaming guide 500 of FIGS. 8A and 8B. Reamer 520 can comprise handle 522 and reaming head 524. Handle 522 can comprise shaft 526, base 528, socket 530 (FIGS. 10A and 10B) and coupler 532. Reaming head 524 can comprise ring 534, spokes 536A-536E and cutting elements 538A-538E. Reamer 520 can be reciprocated along reaming guide 500 and rotated about the axis of reaming guide 500 to remove bone matter from humeral bone 200.

Figures 10A, 10B:
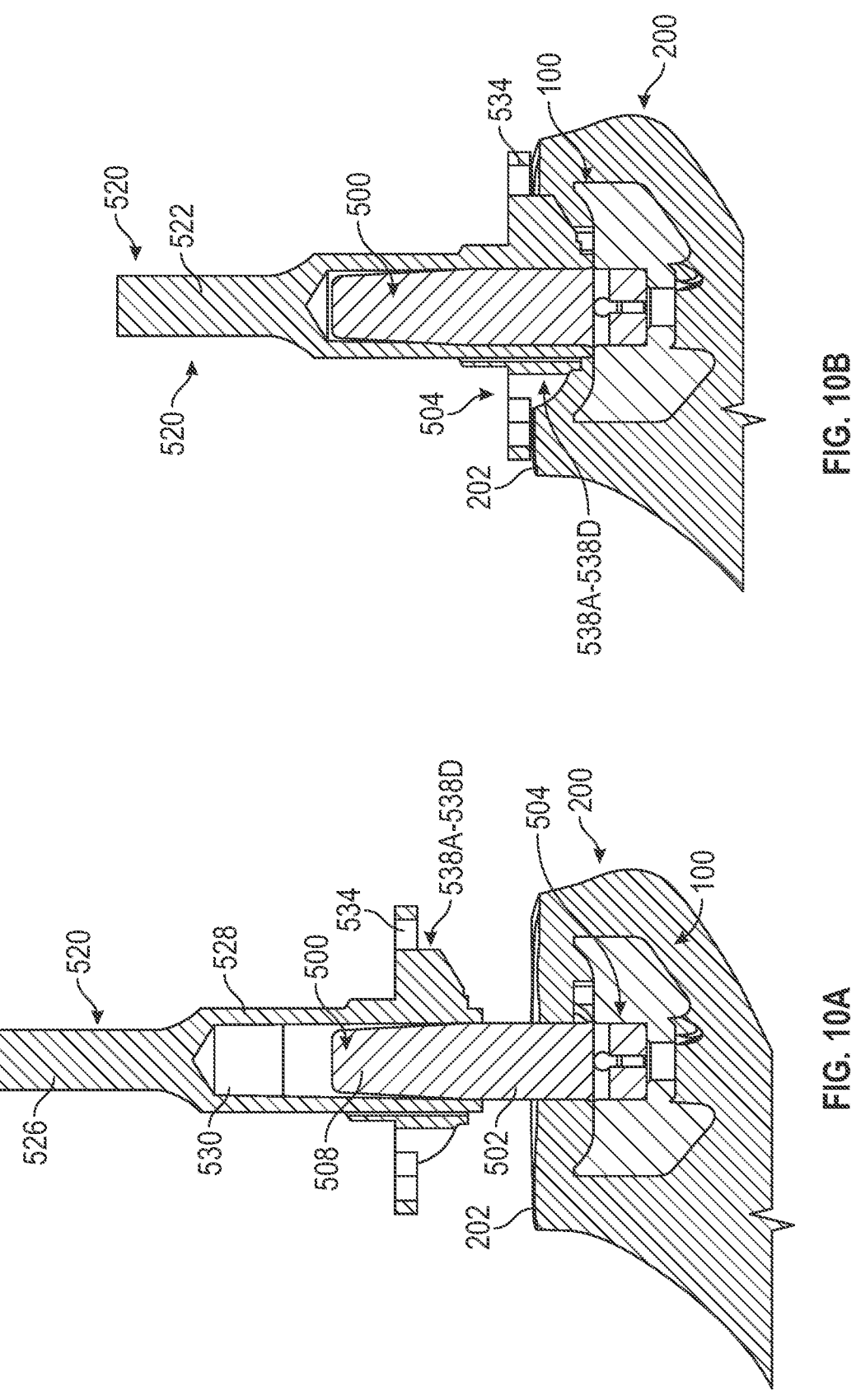
FIG. 10A is a cross-sectional view of the reamer and reaming guide of FIG. 9 with the reamer disposed above a humeral bone.
FIG. 10B is a cross-sectional view of the reamer and reaming guide of FIG. 9 with the reamer extended into the humeral bone.

FIG. 10A is a cross-sectional view of reamer 520 and reaming guide 500 of FIG. 9 with the reamer 520 disposed above humeral bone 200. FIG. 10B is a cross-sectional view of reamer 520 and reaming guide 500 of FIG. 9 with the reamer 520 disposed in humeral bone 200. FIGS. 10A and 10B are discussed concurrently.

Reamer 520 can be positioned superior of reaming guide 500 so that socket 530 aligns with tapered tip 508. Reamer 520 can be pushed down on reaming guide 500 until cutting elements 538A-538D contact resected surface 202. Reamer 520 can be rotated about the axis of shaft 502 to cause cutting elements 538A-538D to remove bone matter. Reamer 520 can be advanced further toward humeral bone 200 until ring 534 contacts resected surface 202. When ring 534 contacts resected surface 202, base 528 of reamer 520 can engage universal broach 100. In particular, base 528 can engage socket 105. As such, the diameter of base 528 can be approximately the same as main body 102 so that reamer 520 can rest on universal broach 100. The shape of cutting elements 538A-538D can correspond to the shape of base 254 on inlay tray 250 to allow inlay tray 250 to rest on the top of bone matter reamed by reaming head 524. Furthermore, as explained in greater detail with reference to FIGS. 11A and 11B, spokes 104A-104E can be shaped to accommodate the presence of reaming head 524. In particular, proximal surfaces of blades 106A-106F can form a bowl-shaped receptacle for reaming head 524. As such, proximal tips 124A, 124B, 124C and 124E (FIGS. 11A and 11GB) of universal broach 100 can be located above the lower portion of reaming head 524 when reaming head 524 is fully advanced.

Figures 11A, 11B:
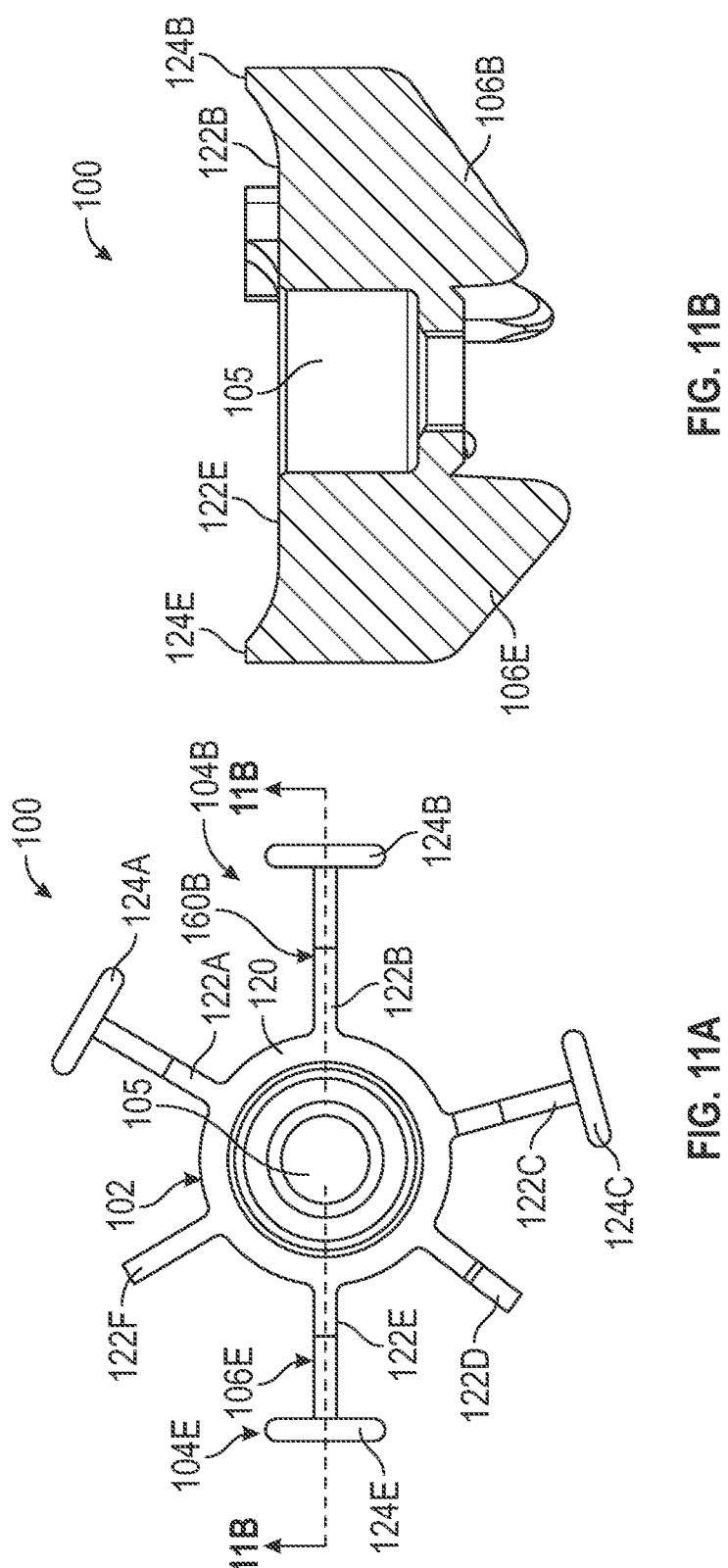
FIGS. 11A and 11B are top and side cross-sectional views of the universal broach of FIG. 1 showing various features that facilitate functioning with a ream guide for performing reaming for an inlay tray configuration.

FIGS. 11A and 11B are top and side cross-sectional views of universal broach 100 of FIG. 1 showing various features that facilitate functioning in cooperation with reaming guide 500 for performing reaming for an inlay tray configuration. As discussed above, universal broach 100 can comprise main body 102 and spokes 104A-104F. Main body 102 can comprise socket 105. Spoke 104A can comprise blade 106A and wing 108A. Spoke 104B can comprise blade 106B and wing 108B. Spoke 104C can comprise blade 106C and wing 108C. Spoke 104D can comprise blade 106D. Spoke 104E can comprise blade 106E and wing 108E. Spoke 104F can comprise blade 106F.

Main body 102 can comprise superior surface 120. Blades 106A-106F can comprise superior surfaces 122A-122F. Additionally, blades 106A, 106B, 106C and 106E can include proximal tips 124A, 124B, 124C and 124E, respectively. Superior surfaces 122A-122F can extend laterally from superior surface 120, e.g., parallel with superior surface 120. Flat portions of superior surfaces 122A-122F can comprise approximately 75% of the diameter of universal broach 100. Radially outer portions of superior surfaces 122A-122F can curve proximally to form proximal tips 124A, 124B, 124C and 124E. As such, flat portions of superior surfaces 122A-122F can be recessed lower into bone matter than proximal tips 124A, 124B, 124C and 124E to allow reaming head 524 to advance lower into bone matter. However, proximal tips 124A, 124B, 124C and 124E can extend along surfaces of bone matter within humeral bone 200 to provide support to the bone matter and prevent damage thereof.

Figure 12:
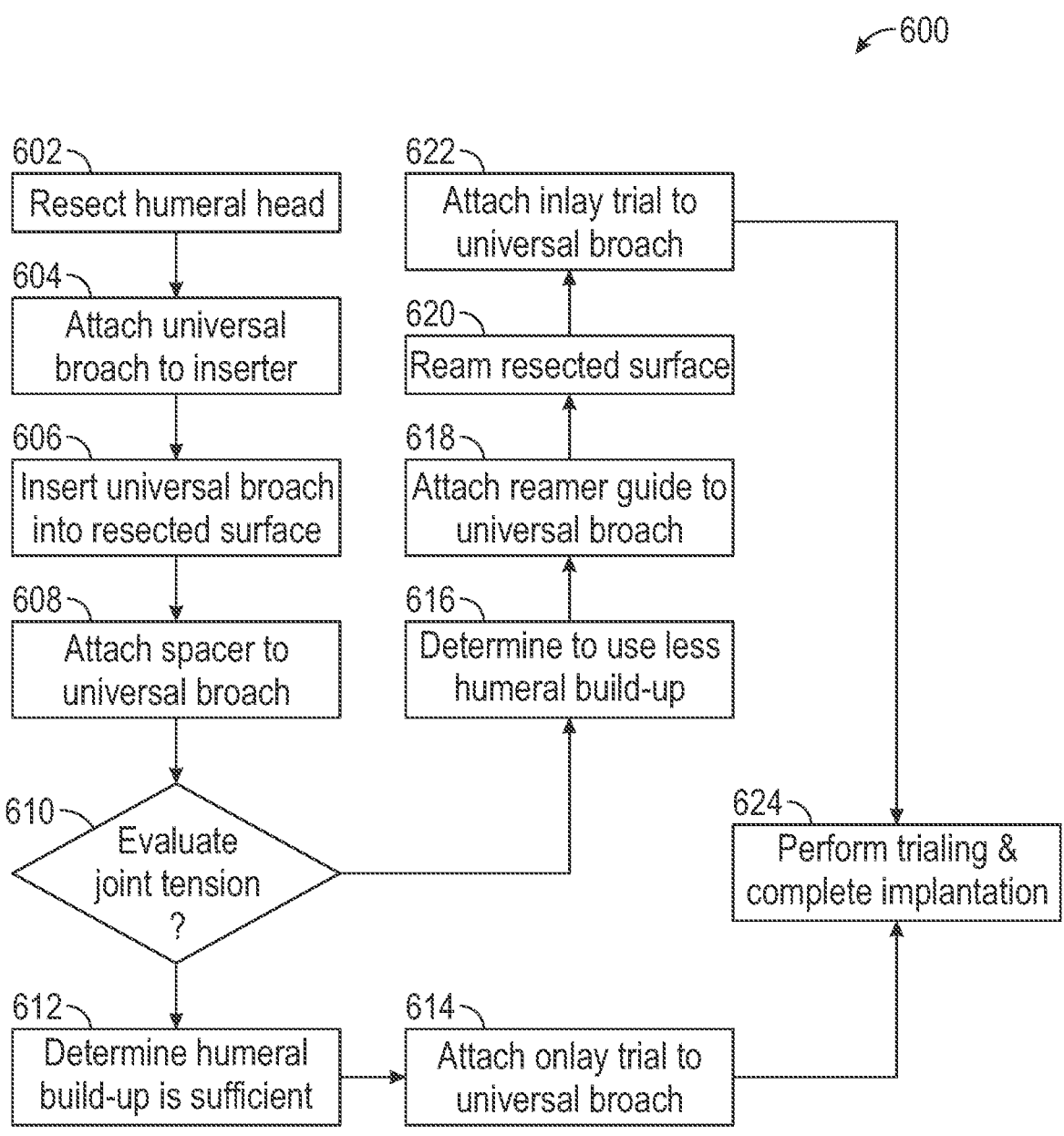
FIG. 12 is a line diagram illustrating operations of methods of the present disclosure relating to implanting inlay or onlay tray configurations using a universal broach of the present disclosure.

FIG. 12 is a line diagram illustrating operations of methods of the present disclosure relating to preparing a humerus bone to receive a prosthetic implant. Method 600 can comprise operation 602 through operation 624 that describe various procedures for implanting a universal broach and determining the laxity of a shoulder joint in order to determine if an inlay tray trail component or an onlay tray trial component will or should be attached to the universal broach. In various examples, additional operations consistent with the devices, systems methods and operations described herein can be included. Likewise, some of operation 602-operation 624 can be omitted.

At operation 602, humeral bone 200 can be resected to form resected surface 202. Resection of humeral bone 200 can be performed using conventional techniques.

At operation 604, universal broach 100 can be attached to inserter 300 of FIG. 4A-5B. For example, universal broach 100 can be inserted into opening 324 so that attachment portion 320 can be inserted into socket 105 of main body 102.

At operation 606, universal broach 100 can be inserted into resected surface 202. For example, the bottom portions of spokes 104A-104F can be pushed into resected surface 202 by pushing inserter 300 until plate 308 engages resected surface 202. Thereafter, handle 304 of inserter 300 can be advanced relative to base 302 to push universal broach 100 further into humeral bone 200 such that the tops of spokes 104A-104F are recessed below resected surface 202. The tops of spokes 104A-104F can be positioned distance D1 below resected surface 202.

At operation 608, spacer 400 (FIG. 6A) can be attached to universal broach 100. For example, attachment portion 408 can be inserted into socket 105 of main body 102.

At operation 610, the tension or laxity of a shoulder joint can be evaluated, assessed or determined. The laxity of the joint, e.g., shoulder joint 700 of FIG. 13, can be determined by assessing the tension in the soft tissue holding the humeral bone on contact with or close proximity to the scapular bone. It is desirable to replicate the tension of a natural shoulder joint where the soft tissues hold the bones in engagement, but the joint is not too tight or difficult to move for the patient. Thus, if spacer 400 cannot fit between the humeral bone and the scapular bone, the soft tissue is holding the joint sufficiently tight such that a shorter or deeper prosthetic implant can be used, such as an inlay tray. However, if spacer 400 can readily fit between the humeral bone and the scapular bone, the soft tissue is not holding the joint sufficiently tight such that a taller or shallower prosthetic implant can be used, such as an onlay tray.

At operation 612, a surgeon can determine that spacer 400 can readily fit between the humeral bone and the scapular bone. As such, the surgeon can determine that the soft tissue is not holding a component having the thickness of the spacer joint tight enough to replicate a natural joint. As such, the surgeon can determine that a taller or thicker (relative to joint gap height) humeral head build-up, e.g., prosthetic implant, can be used, such as onlay tray 206, if desired. For example, the tightness of the joint may be that either inlay or onlay trays may work, depending on construct of T1-T4.

At operation 614, the surgeon can attach onlay tray 206 to universal broach 100. Thus, spacer 400 can be removed from universal broach 100 and attachment portion 216 of onlay tray 206 can be inserted into socket 105 of main body 102. Thereafter, the surgeon can complete trialing of the joint using universal broach 100 and onlay tray 206 in order to build a final construct that will be implanted into the patient, such as at operation 624.

At operation 616, the surgeon can determine that spacer 400 cannot fit between the humeral bone and the scapular bone, or cannot fit without using undue force. As such, the surgeon can determine that the soft tissue is holding the joint sufficiently tight such that a shorter or thinner (relative to joint gap height) humeral build-up, e.g., prosthetic implant, can be used such as inlay tray 250, if desired. For example, the tightness of the joint may be that either inlay or onlay trays may work, depending on construct of T1-T4.

At operation 618, a surgeon can attach reaming guide 500 to universal broach 100. Thus, spacer 400 can be removed from universal broach 100 and attachment portion 504 of reaming guide 500 can be inserted into socket 105 of main body 102.

At operation 620, resected surface 202 can be reamed. Reamer 520 can be advanced over reaming guide 500 to engage reaming head 524 with resected surface 202.

At operation 622, the surgeon can attach inlay tray 250 to universal broach 100. Thus, reaming guide 500 can be removed from universal broach 100 and attachment portion 258 of inlay tray 250 can be inserted into socket 105 of main body 102. Thereafter, the surgeon can complete trialing of the joint using universal broach 100 and inlay tray 250 in order to build a final construct that will be implanted into the patient, such as at operation 624.

After the surgical procedure is performed, universal broach 100 is removed from the patient and a final prosthetic implant is left within the anatomy to function as a prosthetic joint. The final prosthetic implant having a shape similar to that of universal broach plus one of onlay tray 206 and prosthetic bearing component 230 or inlay tray 250 and prosthetic bearing component 270. The access incision in the patient can be closed up with appropriate suturing or the like, leaving the prosthetic implant within the shoulder joint.

FIG. 13 is a schematic view of shoulder joint 700 configured to receive a total shoulder joint replacement in a reverse shoulder configuration, in an example of the present disclosure. Shoulder joint 700 can comprise scapula 702 and humerus 704. Shoulder joint 700 is an example of a joint in which universal broach 100 of FIGS. 1-11B can be used.

Prosthetic glenoid 706 can be implanted into scapula 702. Prosthetic bearing 708 can be implanted in humerus 704. Prosthetic glenoid 706 can be attached to anchor device 710. Prosthetic bearing 708 can comprise articulation component 712, tray 714 and anchor component 716. In the illustrated example of FIG. 13, anchor component 716 comprises stem 718. Universal broach concepts of the present disclosure can be applied to broaches used with stemmed or stemless components. In examples, tray 714 can comprise onlay tray 206 or inlay tray 250 and stem 718 can be omitted.

As discussed herein, the laxity or tension between scapula 702 and humerus 704 can determine which type of prosthetic construct is used in shoulder joint 700. In particular, the laxity or tension between scapula 702 and humerus 704 can determine if onlay tray 206 or inlay tray 250 is used after prosthetic glenoid 706 is installed and resected surface 720 is produced. As such, gap G can exist between the resected surface 720 and the top of prosthetic glenoid 706 when implanted into scapula 702. In the present application, if spacer 400 fits within gap G, e.g., gap G is thicker than distance D4, then onlay tray 206 can be used, and if spacer 400 does not fit within gap G, e.g., gap G is thinner than distance D4 minus D1, then inlay tray 250 can be used. Additionally, if spacer 400 fits within gap G, but shoulder joint 700 is tight, e.g., there is excessive binding between prosthetic glenoid 706 and spacer 400, then inlay tray 250 can be used.

Figures 14A, 14B:
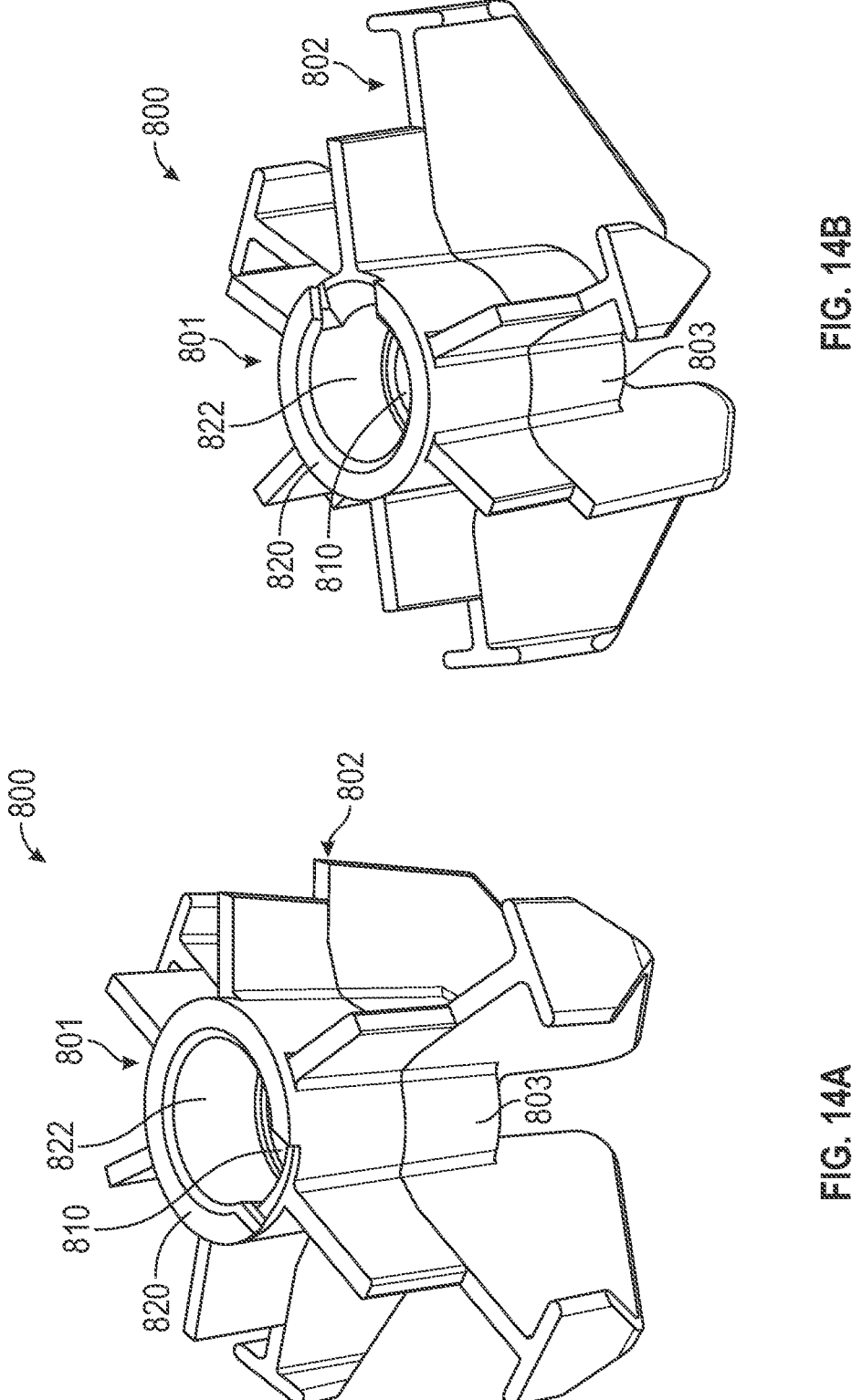
FIGS. 14A and 14B are perspective views of a universal broach assembly comprising a universal broach proximal body and a universal broach distal body.
Figures 15, 16:
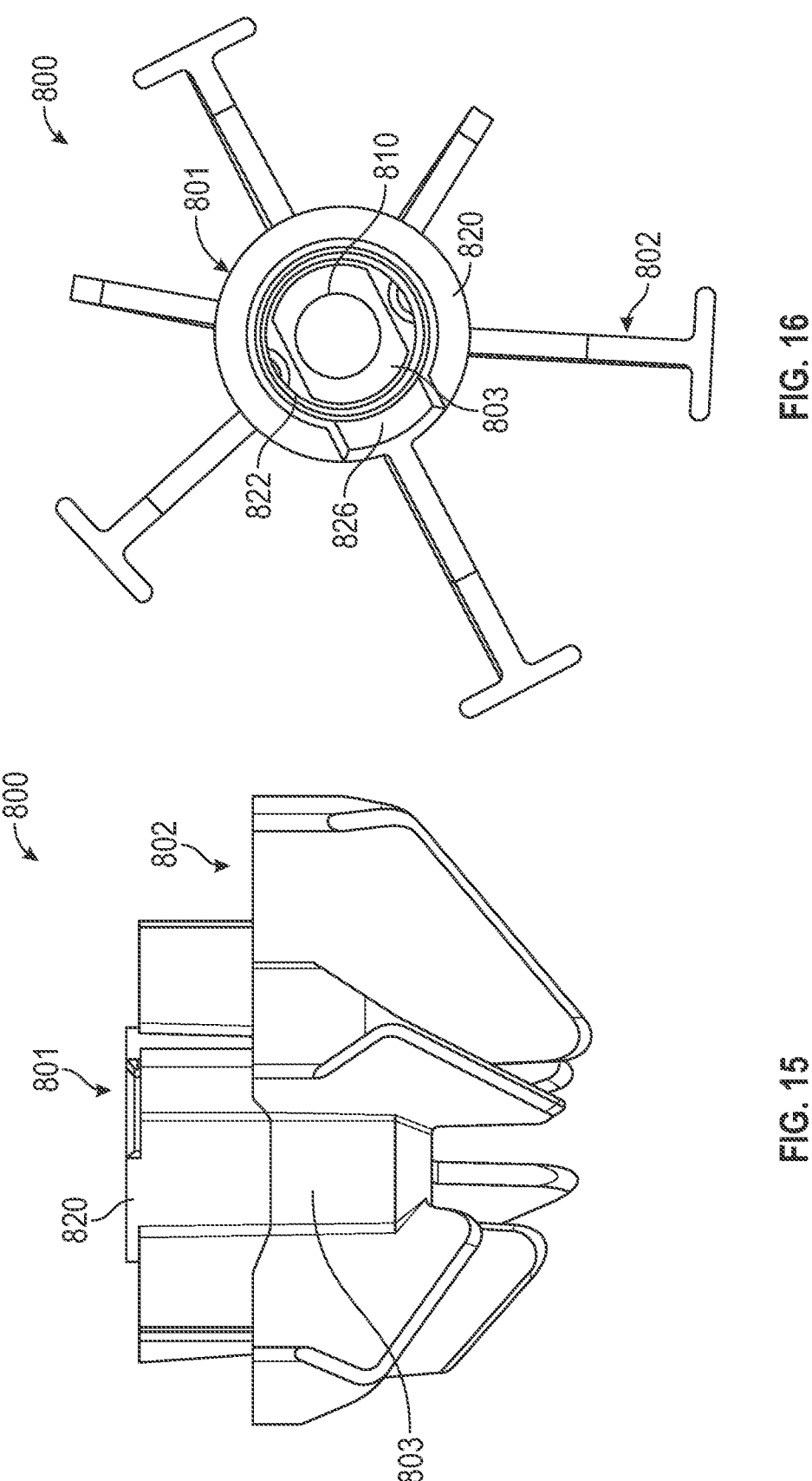
FIG. 15 is a side view of the universal broach assembly of FIGS. 14A and 14B.
FIG. 16 is a top view of the universal broach assembly of FIGS. 14A and 14B.
Figure 17B:
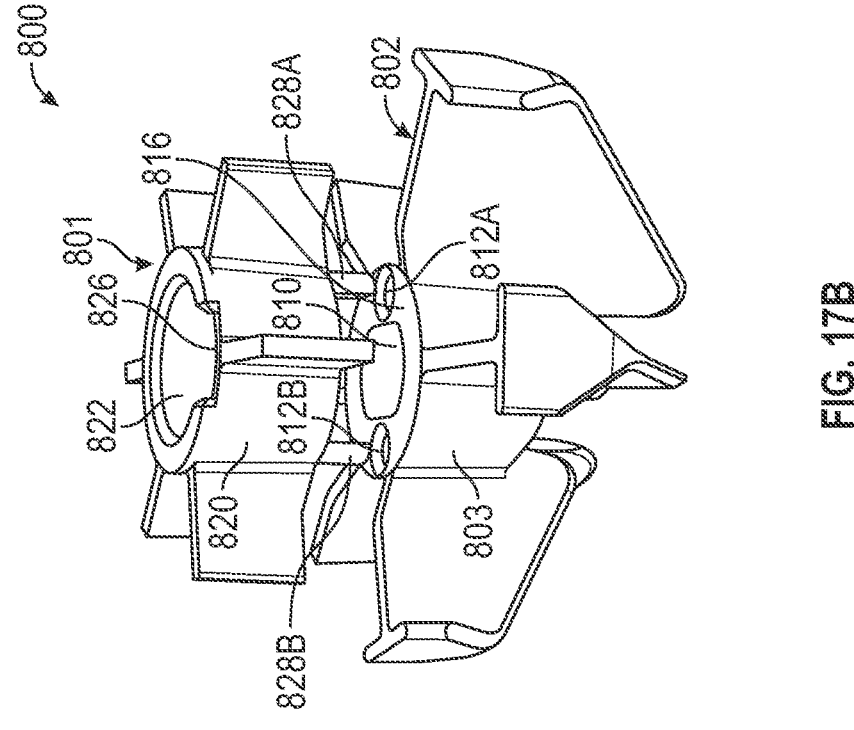
FIGS. 17A and 17B are perspective views of the universal broach proximal body exploded from the universal broach distal body.
Figure 17A:
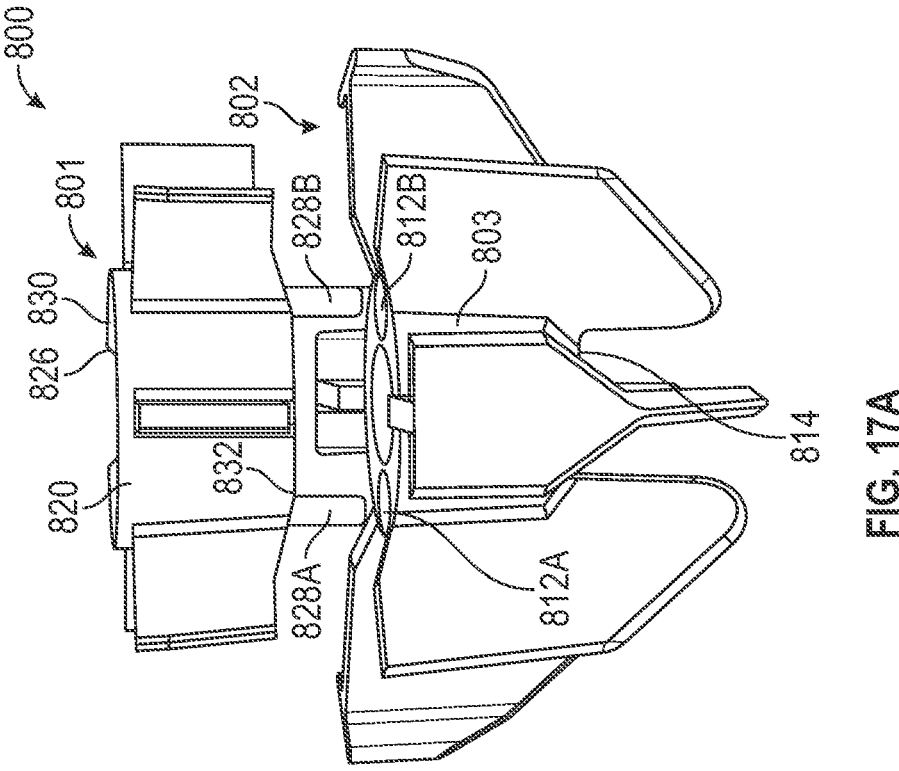

FIGS. 14A and 14B are perspective views of universal broach assembly 800 comprising universal broach distal body 802 assembled with universal broach proximal body 801. FIG. 15 is a side view of universal broach distal body 802 and universal broach proximal body 801 of FIGS. 14A and 14B. FIG. 16 is a top view of universal broach distal body 802 and universal broach proximal body 801 of FIGS. 14A and 14B. FIGS. 17A and 17B are perspective views of universal broach proximal body 801 exploded from universal broach distal body 802. FIGS. 14A-17B are discussed concurrently.

Universal broach distal body 802 can comprise a broaching body and universal broach proximal body 801 can comprise a spacer body. Universal broach distal body 802 can be configured to perform broaching procedures for both inlay and onlay operations. Universal broach distal body 802 can be used with universal broach proximal body 801 for onlay and inlay operations. Universal broach distal body 802 can be used to broach bone matter with universal broach proximal body 801 attached. For onlay procedures, universal broach proximal body 801 can be left attached to universal broach distal body 802 to perform trialing using universal broach distal body 802. For inlay procedures, universal broach proximal body 801 can be removed from universal broach distal body 802 to perform trialing using universal broach distal body 802.

Universal broach distal body 802 can be configured similarly to universal broach 100 of FIG. 1 discussed above to cut or displace bone matter in a particular pattern to receive an anchor component of a prosthetic implant. Spokes 804A-804F can be spaced at intervals, either different or the same, so that an overall interval pattern is achieved. Universal broach proximal body 801 can be used with different sized universal broach distal bodies 802. For example, universal broach distal body 802 can have a first size for use with a first sized implant. Other sized universal broaches can be attached to universal broach proximal body 801 for different sized bones, as discussed with reference to FIGS. 26A-27B. For example, other universal broaches can have broaching elements, e.g., spokes 804A-804F of FIG. 19, with shorter lengths such that the overall diameters or the universal broaches can be used with smaller implants. However, the size of main body 803 can be kept the same for the different sized broaching elements so that universal broach proximal body 801 can be used with the different sized universal broach distal bodies 802.

Universal broach distal body 802 and universal broach proximal body 801 can be used with a modified version of inserter 300 (FIGS. 32 and 33) with attachment portion 320 modified to accommodate universal broach proximal body 801 to insert universal broach distal body 802 a fixed distance below a resected bone surface. In examples, universal broach proximal body 801 can have a thickness equal to distance D1 (FIGS. 2A and 2B) to facilitate evaluation of bone matter and compatibility with onlay tray 206 (FIG. 2B) and inlay tray 250 (FIG. 3B). Universal broach proximal body 801 and universal broach distal body 802 can be used with a modified version of spacer 400 (FIG. 6A) without attachment portion 408 to evaluate joint laxity.

Figure 18:
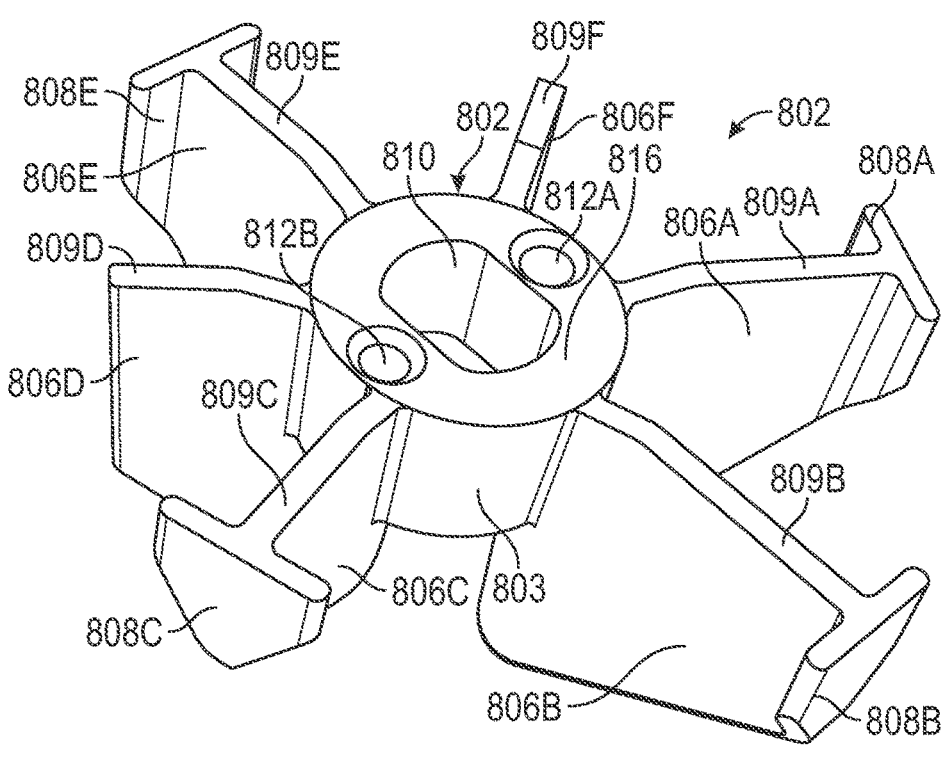
FIGS. 18 and 19 are perspective top and bottom views of a universal broach distal body of the present disclosure, respectively.
Figure 19:
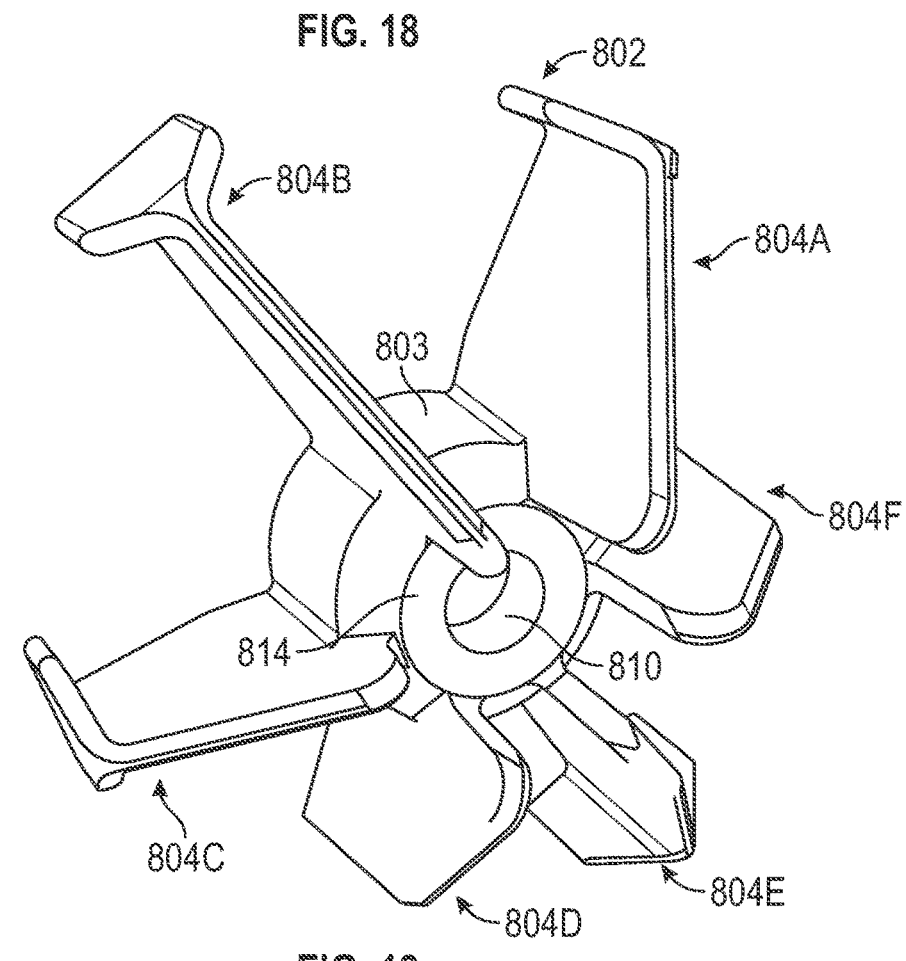
Figures 20, 21:
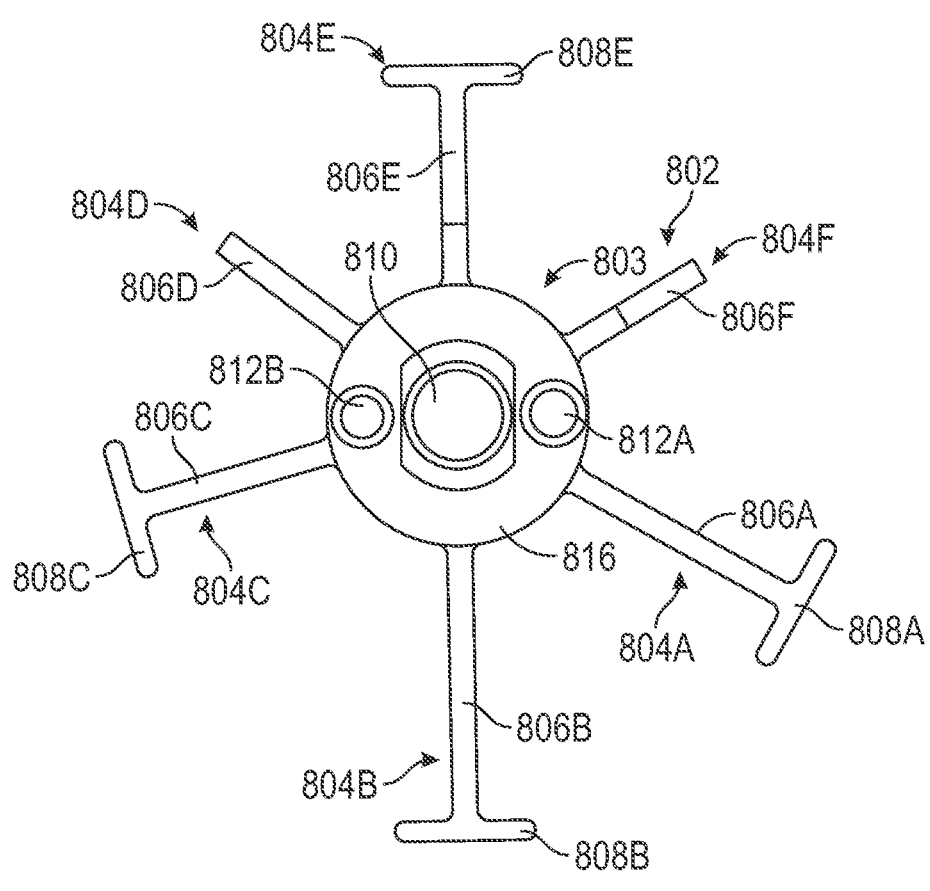
FIGS. 20 and 21 are side and top views of the universal broach distal body of FIGS. 18 and 19, respectively.

FIGS. 18 and 19 are perspective top and bottom views of universal broach distal body 802 of the present disclosure, respectively. FIGS. 20 and 21 are side and top views of universal broach distal body 802 of FIGS. 18 and 19, respectively. FIGS. 18-21 are discussed concurrently.

Universal broach distal body 802 can comprise main body 803 and spokes 804A-804F. Spoke 804A can comprise blade 806A and wing 808A. Spoke 804B can comprise blade 806B and wing 808B. Spoke 804C can comprise blade 806C and wing 808C. Spoke 804D can comprise blade 806D. Spoke 804E can comprise blade 806E and wing 808E. Spoke 804F can comprise blade 806F. Main body can comprise socket 810 and ports 812A and 812B.

Spokes 804A-804F can be configured to broach bone as is described above with reference to spokes 104A-104F of universal broach 100 of FIG. 1. Blades 806A-806F can project radially from main body 803 and can extend distally of distal surface 814. Blades 806A-806F can extend proximally of proximal surface 816. However, the radial inner ends of blades 806A-806F at main body 803 can be reduced in height, such as by including a chamfer or the like, to join with proximal surface 816. As such, the proximal or top side of universal broach distal body 802 can have depression 817 extending inward to receive universal broach proximal body 801. Blades 806A-806F can, therefore, form a bowl-shaped receptacle, as discussed herein. Thus, as compared to universal broach 100 of FIG. 1, blades 806A-806F can have radially extending surfaces 809A-809F that are at the same horizontal level as wings 808A, 808B, 808C and 808E. As discussed in greater detail below with reference to FIG. 33, radially extending surfaces 809A-809F of blades 806A-806F can be elevated from main body 803 to facilitate transfer of force from shaft 318 of inserter 300 (FIGS. 32 and 33) to universal broach distal body 802 through universal broach proximal body 801.

Proximal surface 816 can include ports 812A and 812B to facilitate coupling with universal broach proximal body 801. Ports 812A and 812B can comprise cylindrical bores extending into main body 803. In examples, ports 812A and 812B can comprise blind-end bores that extend into proximal surface 816 and stop short of distal surface 814. Ports 812A and 812B can be located one-hundred-eighty degrees away from each other within main body 803. Ports 812A and 812B can allow for two-way coupling with pegs 828A and 828B of universal broach proximal body 801. That is, pegs 828A and 828B of universal broach proximal body 801 can couple to ports 812A and 812B in two orientations. Proximal surface 816 can be flat to allow distal surface 832 (FIG. 24) of universal broach proximal body 801 to mate flush. FIGS. 18-20 show one version of ports 812A and 812, but other configurations can be used. For example, ports 812A and 812B can have other cross-sectional shapes, such as square, and can be located at other circumferential positions from each other, such as ninety degrees.

Figure 30:
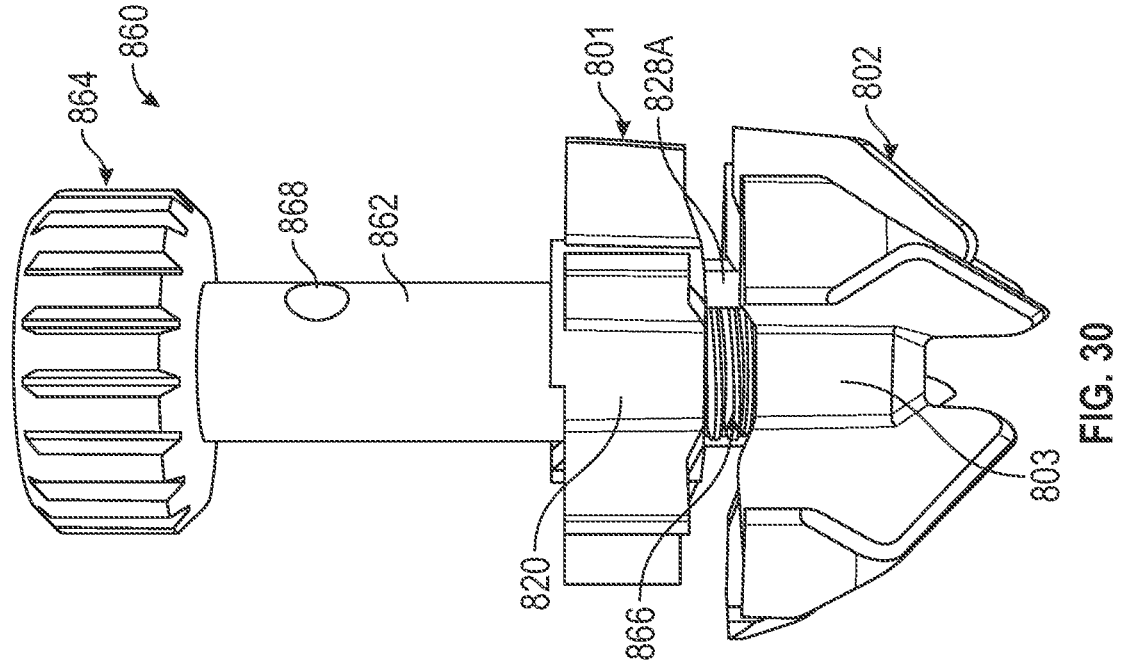
FIG. 30 is a perspective view of the removal tool advanced to separate the universal broach proximal body from the universal broach distal body.

Socket 810 can have an upper portion and a lower portion. In examples, the upper portion can comprise an oblong slot having opposed arcuate walls connecting opposed straight walls. The opposed walls forming the upper portion can form an opening smaller in size than tip 866 of removal tool 860, as shown in FIG. 30, to allow shaft 862 of removal tool 860 to push against universal broach distal body 802. In examples, the upper portion of socket 810 can comprise a cylindrical bore. The upper portion of socket 810 can be configured similarly to socket 105 of universal broach 100 of FIG. 1. Socket 810 can be configured to mate with attachment portion 504 of reaming guide 500 (FIGS. 10A and 10B) and to mate with attachment portion 320 of inserter 300 (FIGS. 4A and 4B). The upper portion of socket 810 can additionally be configured to mate with attachment portion 216 of onlay tray 206 (FIG. 2B) and attachment portion 258 of inlay tray 250 (FIG. 3B). The upper portion can transition into the lower portion via a bowl shape. The lower portion can comprise a cylindrical bore having a straight sidewall. The lower cylindrical bore can allow for biological matter and instruments to pass through universal broach distal body 802 and to allow for visual inspection of biological matter distal of universal broach distal body 802.

Figure 22:
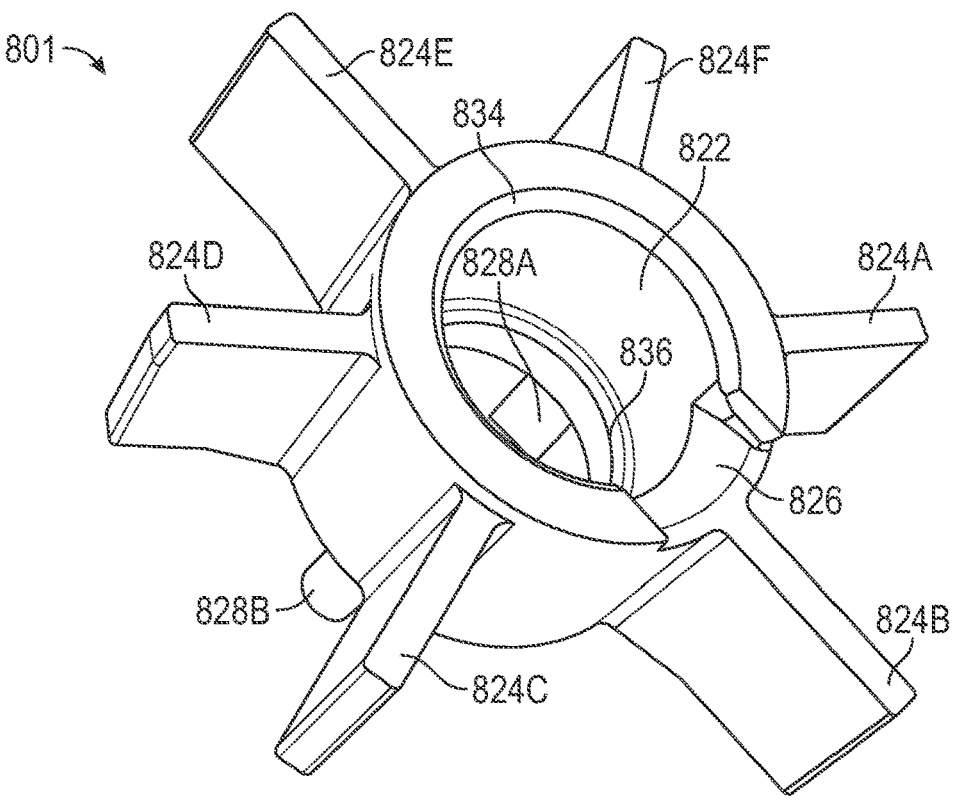
FIGS. 22 and 23 are perspective top and bottom views of a universal broach proximal body of the present disclosure, respectively.
Figure 23:
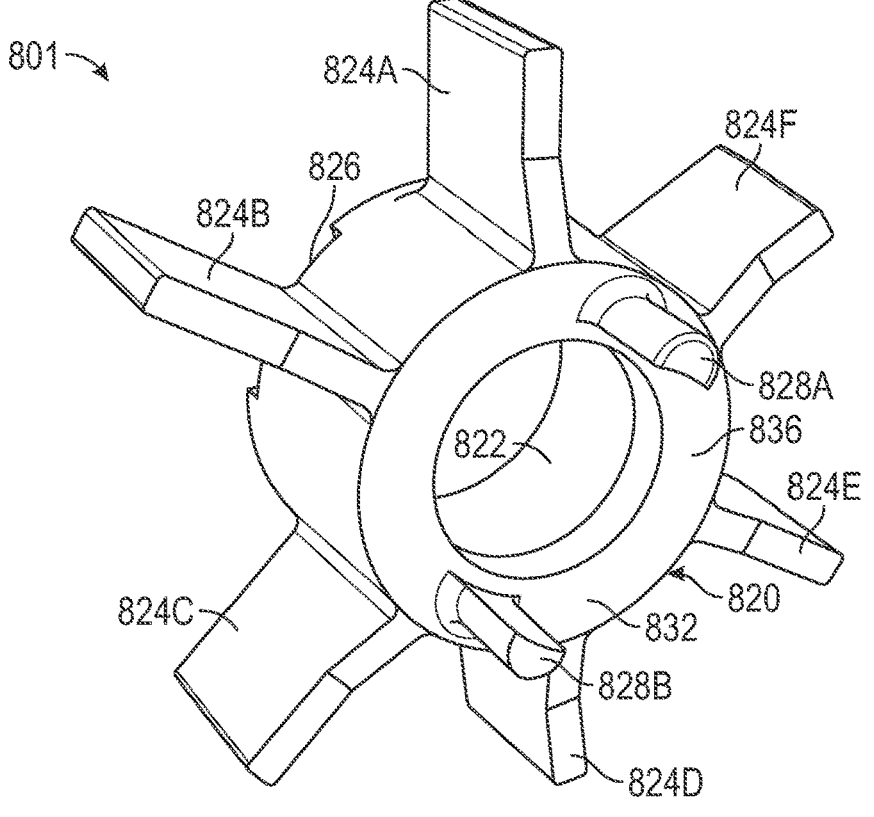
Figure 24:
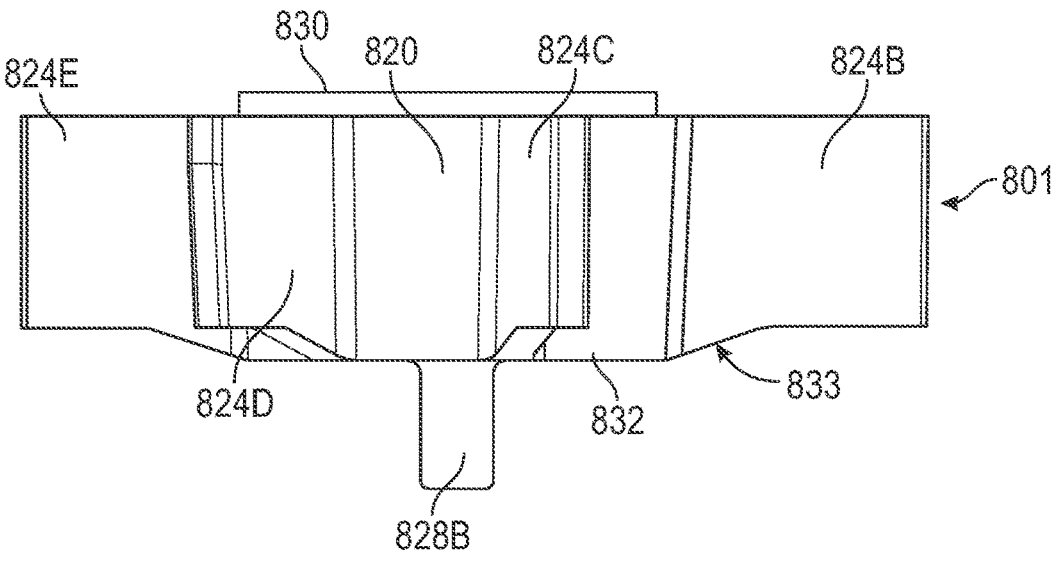
FIGS. 24 and 25 are side and top views of the universal broach proximal body of FIGS. 22 and 23, respectively.
Figure 25:
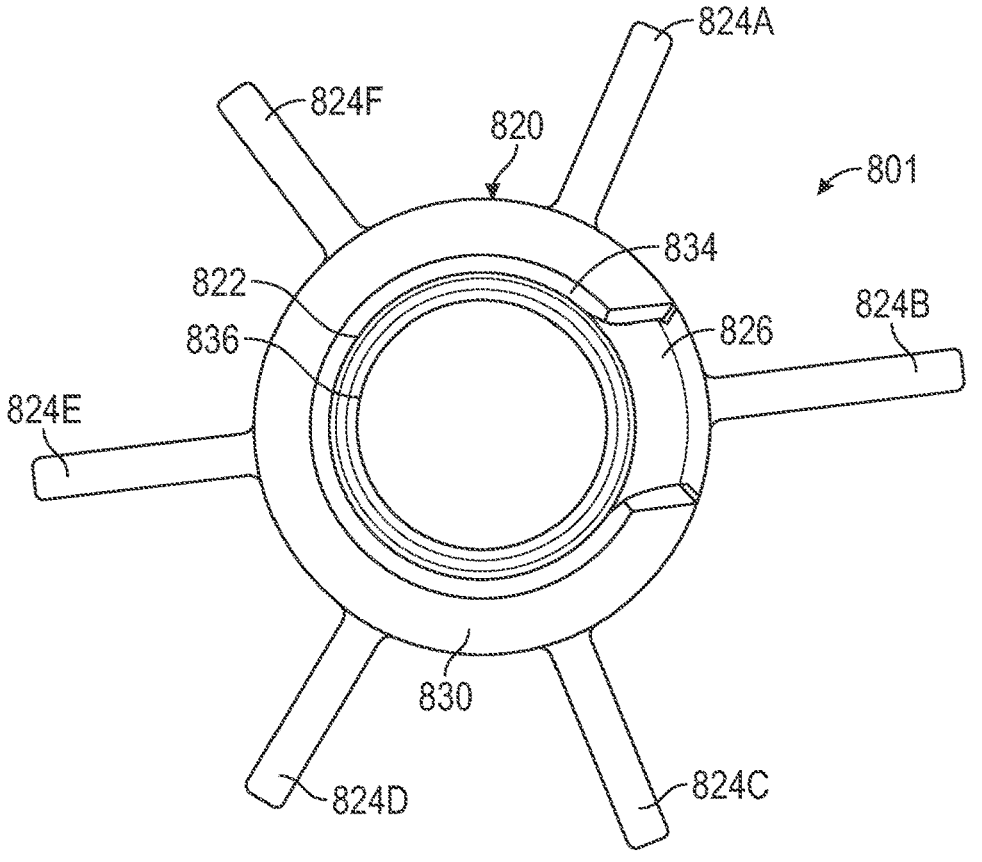

FIGS. 22 and 23 are perspective top and bottom views of universal broach proximal body 801 of the present disclosure, respectively. FIGS. 24 and 25 are side and top views of universal broach proximal body 801 of FIGS. 22 and 23, respectively. FIGS. 22-25 are discussed concurrently.

Universal broach proximal body 801 can comprise main body 820, socket 822, spokes 824A-824F, notch 826 and pegs 828A and 828B. Main body 820 can comprise an annular ring to mate with main body 803 of universal broach distal body 802 of FIGS. 18-21. Proximal surface 830 of main body 820 can be flat and can include notch 826. Distal surface 832 can be flat to facilitate mating with proximal surface 816 of main body 803 (FIG. 18). Distal surface 832 can extend more distally than spokes 824A-824F to form extension 833 for mating with depression 817 (FIG. 21) of universal broach distal body 802. Pegs 828A and 828B can extend from distal surface 832 and can be arranged to align with ports 812A and 812B, respectively. Pegs 828A and 828B can comprise semi-circular extensions having a length equal to or shorter than ports 812A and 812B. The outer diameter of pegs 828A and 828B can have outer dimensions so that pegs 828A and 828B fit snug within ports 812A and 812B to prevent movement or jostling therebetween.

Spokes 824A-824F can have different lengths. The lengths of spokes 824A-824F can vary based on the lengths of spokes 804A-804F of universal broach distal body 802. In examples, spoke 824B, 824C and spoke 824E can be longer than spokes 824A, 824D and 824F. Ports 812A and 812B can be arranged to receive pegs 828A and 828B in two different ways so that spokes 824A, 824C and 824E are disposed to sit atop those of spokes 804A-804F that have an equal or longer length. In various examples, universal broach proximal body 801 can be configured to attach to any size of universal broach distal body 802 so that none of spokes 824A-824F will extend beyond any of spokes 804A-804F. In examples, spokes 824A-824F can be configured to have the same lengths as spokes 804A-804F for the smallest sized universal broach distal body 802, such as universal broach distal body 802B of FIG. 27A.

Figure 31:
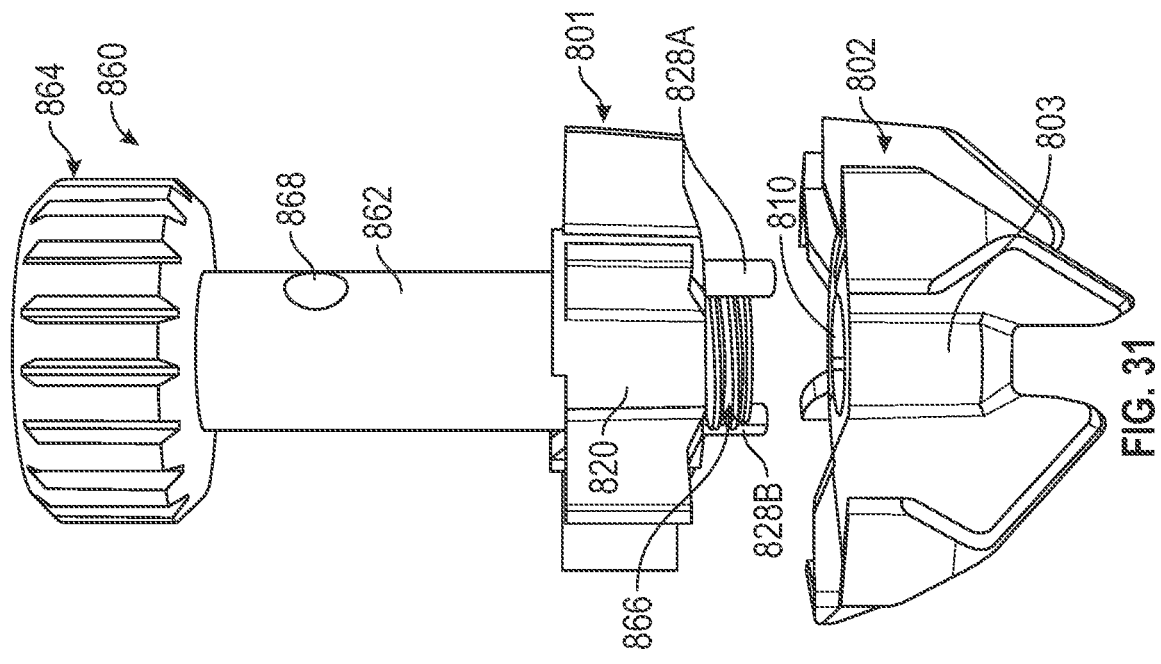
FIG. 31 is a perspective view of the removal tool and universal broach proximal body separated from the universal broach distal body.
Figures 32, 33:
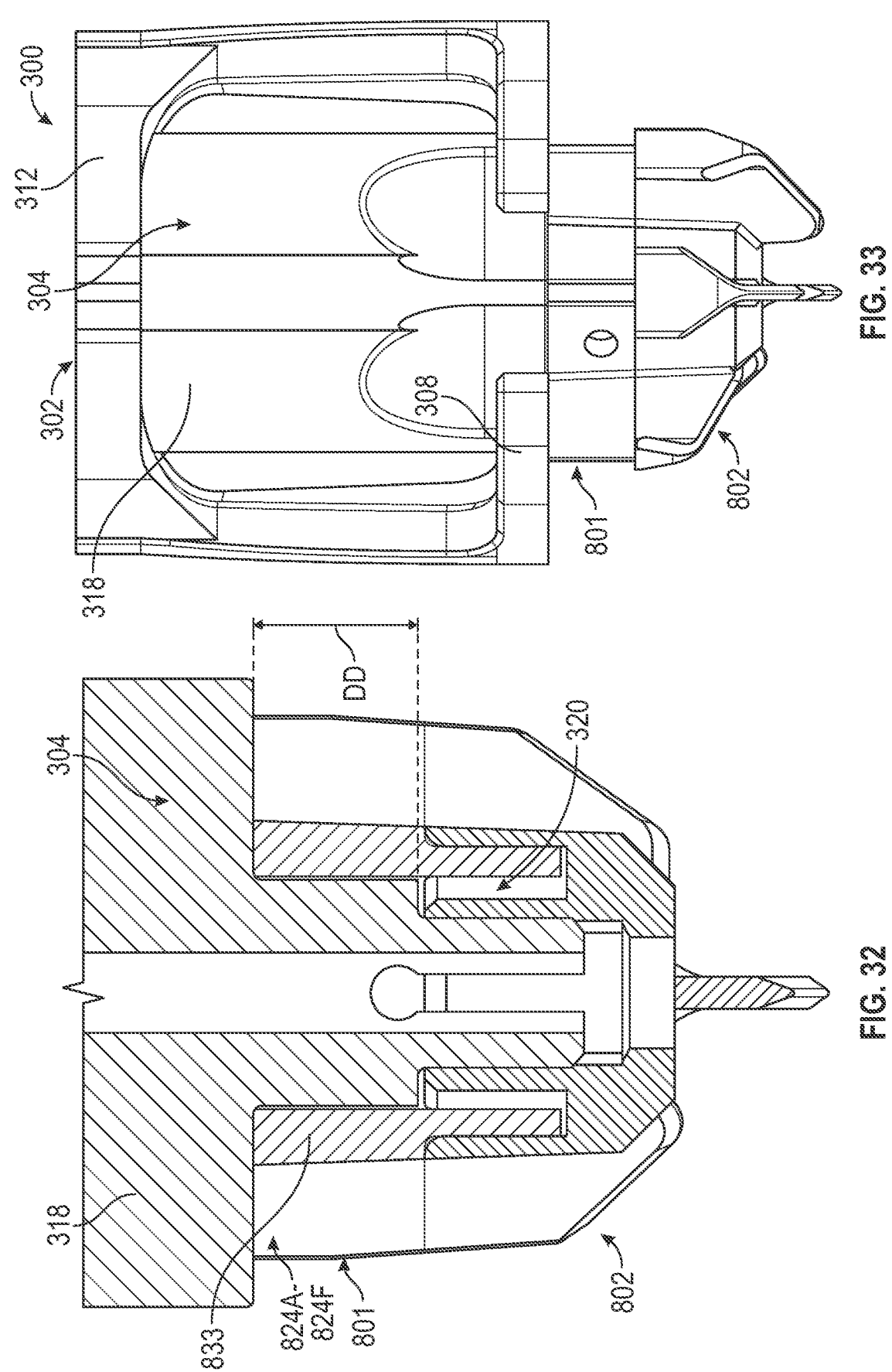
FIG. 32 is a cross-sectional view of the universal broach proximal bodies and the universal broach distal bodies of FIGS. 14A-27B attached to an insertion tool.
FIG. 33 is a side view of the insertion tool of FIG. 21 actuated to push the universal broach assembly into bone.

Proximal surface 830 can be flat and can be configured to engage with shaft 318 of inserter 300, as shown in FIG. 33. Bevel 834 can be positioned between proximal surface 830 and socket 822. Bevel 834 can be configured to provide a surface to guide engagement of tip 866 of removal tool 860, as shown in FIG. 30, into socket 822. Socket 822 can be sized to allow shaft 862 of removal tool 860 to pass therethrough. However, socket 822 can include flange 836 to engage with shaft 862. In examples, shaft 862 and flange 836 can have complimentary threading to allow for a threaded engagement therebetween. Thus, as shown in FIGS. 30 and 31, shaft 862 can be passed through universal broach proximal body 801 via threaded engagement. Socket 822 and flange 836 can additionally be sized to allow extension 833 (FIG. 32) of inserter 300 to pass therethrough. Socket 822 can be configured to mate with attachment portion 216 of onlay tray 206 (FIG. 2B) wherein stem 210 is shortened to accommodate universal broach proximal body 801 being closer to the resected bone surface.

FIG. 26A is a side view of universal broach proximal body 801 and universal broach distal body 802A of a first size. FIG. 26B is a top view of universal broach distal body 802A and universal broach proximal body 801 of FIG. 26A inserted into resected surface 850A of humeral bone 852A. Universal broach distal body 802A can comprise main body 803A as well as spokes similar to spokes 804A-804F of universal broach distal body 802.

In the illustrated example, universal broach distal body 802A can be the same size as universal broach distal body 802 of FIGS. 18-21. Universal broach proximal body 801 can be configured to sit atop universal broach distal body 802A with pegs 828A and 828B being aligned within ports, e.g., ports 812A and 812B, within universal broach distal body 802A. As can be seen in FIG. 26A, universal broach distal body 802A can have a larger outer diameter than universal broach proximal body 801. As can be seen in FIG. 26B, spokes 804A-804F of universal broach distal body 802A can extend beyond spokes 824A-824F of universal broach proximal body 801.

FIG. 27A is a side view of universal broach proximal body 801 and universal broach distal body 802B of a second size. FIG. 27B is a top view of universal broach distal body 802B and universal broach proximal body 801 of FIG. 27A inserted into resected surface 850B of humeral bone 852B. Universal broach distal body 802B can comprise main body 803B as well as spokes similar to spokes 804A-804F of universal broach distal body 802, but that are shorter in length and smaller in height.

In the illustrated example, universal broach distal body 802B can be smaller than universal broach distal body 802 of FIGS. 18-21. Universal broach proximal body 801 can be configured to sit atop universal broach distal body 802B with pegs 828A and 828B being aligned within ports, e.g., ports 812A and 812B, within universal broach distal body 802B. As can be seen in FIG. 27A, universal broach distal body 802B can have the same outer diameter as universal broach proximal body 801. As can be seen in FIG. 27B, spokes 804A-804F of universal broach distal body 802B can extend the same distances as spokes 824A-824F of universal broach proximal body 801.

Universal broach distal bodies 802A and 802B can be configured similarly to universal broach distal body 802 to couple with universal broach proximal body 801 and to cut bone, but can have different cutting pattern scales. The spacing intervals between the spokes of universal broach distal bodies 802A and 802B can be the same to form the same interval pattern to facilitate compatibility with the spokes of universal broach proximal body 801. A plurality of intermittently sized universal broach assemblies 800 can be provided having sizes between universal broach distal body 802A and universal broach distal body 802B. Main bodies 803A and 802B can be configured similarly as main body 803 to maintain compatibility with universal broach proximal body 801. But spokes 804A-824F can be scaled up or down, e.g., be longer or shorter and/or taller or shorter, to produce different broaching patterns in bone for different sized implants and different sized bones. A set of universal broach distal bodies 802 can be provided that correspond to different sized humeral implants.

The disposition of spokes 824A-824F on top of spokes 804A-804F provide a surgeon a way to visualize the relationship of spokes 804A-804F to the outer cortical bone wall of humeral bones 852A and 852B, as well as the proximity of spokes 824A-824F to resected surfaces 850A and 850B. Thus, a surgeon can evaluate the positioning of universal broach distal bodies 802A and 802B in bone and the depth of universal broach distal bodies 802A and 802B. The later of which can help evaluate if an onlay or an inlay implant is needed or desired.

Figure 28:
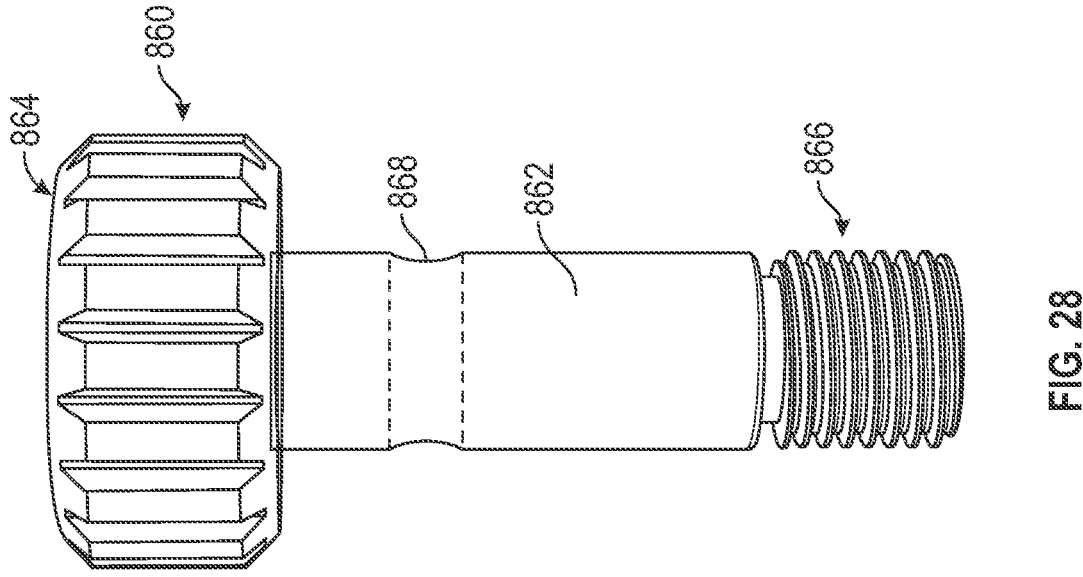
FIG. 28 is a side view of a removal tool suitable for use with the universal broach assemblies of FIGS. 14A-27B.

FIG. 28 is a perspective view of removal tool 860 suitable for use with universal broach proximal body 801 and universal broach distal body 802 of FIGS. 14A-27B. Removal tool 860 can comprise shaft 862, head 864, tip 866 and bore 868. Head 864 can comprise a knob having furrowing to facilitate gripping and rotation of shaft 862. Shaft 862 can provide sufficient length to allow tip 866 to pass into the anatomy and through universal broach proximal body 801 to engage universal broach distal body 802. Tip 866 can comprise threading to engage with flange 836 (FIG. 25), as discussed herein. Bores 868 and bore 870 (FIG. 29) can allow for the passage of other things through removal tool 860, such as fluids or pins, etc. For example, a pin can be placed in bore 868 to facilitate rotation of shaft 862. Additionally, bore 870 can comprise a blind end bore having threads to allow for coupling to a slap hammer device to facilitate removal of universal broach proximal body 801 from universal broach distal body 802 if desired or needed. In examples, removal tool 860 can be fabricated of stainless steel.

Figure 29:
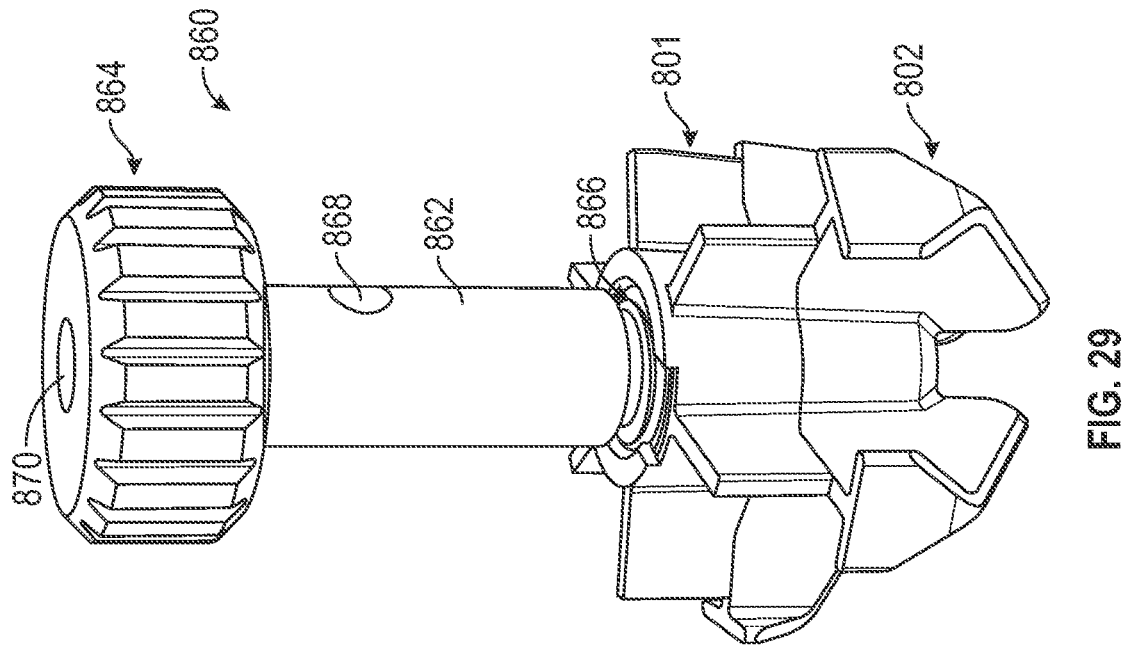
FIG. 29 is a perspective view of the removal tool attached to a universal broach assembly.

FIG. 29 is a perspective view of removal tool 860 attached to universal broach distal body 802 assembled with universal broach proximal body 801. Tip 866 of removal tool can be inserted into socket 822 of universal broach proximal body 801 to engage universal broach distal body 802. Head 864 can be rotated to rotate shaft 862 to engage threading on tip 866 with threading on flange 836 (FIG. 25).

FIG. 30 is a side view of removal tool 860 advanced to separate universal broach proximal body 801 from universal broach distal body 802. Head 864 can continue to be rotated to rotate shaft 862 to further advance threading on tip 866 through threading on flange 836 (FIG. 25). As tip 866 advances through universal broach proximal body 801, the distal end of tip 866 can engage and push against proximal surface 816 of universal broach distal body 802. Engagement of pegs 828A and 828B with ports 812A and 812B can prevent rotation of universal broach proximal body 801. Thus, universal broach proximal body 801 can be induced to ride up along threading of tip 866 as tip 866 rotates against universal broach distal body 802.

FIG. 31 is a perspective view of removal tool 860 and universal broach proximal body 801 separated from universal broach distal body 802. Head 864 can continue to be rotated to rotate shaft 862 to further advance threading on tip 866 through threading on flange 836 (FIG. 25). Universal broach proximal body 801 can continue to ride up along threading of tip 866 to fully disengage pegs 828A and 828B from ports 812A and 812B. Removal tool 860 can be pulled away from the anatomy carrying universal broach proximal body 801 along with it. Thus, removal tool 860 can facilitate separation of universal broach proximal body 801 from universal broach, such as by overcoming friction between pegs 828A and 828B and ports 812A and 812B as well as friction between spokes 824A-824F and bone matter.

FIG. 32 is a cross-sectional view of universal broach proximal body 801 and universal broach distal body 802 of FIGS. 14A-27B attached to inserter 300. FIG. 33 is a side view of inserter 300 of FIG. 21 actuated to push universal broach proximal body 801 and universal broach distal body 802 into bone.

Inserter 300 of FIGS. 32 and 33 can be configured similarly as inserter 300 of FIGS. 4A-5B except that extension 833 can be longer than extension 321. Extension 833 can position attachment portion 320 distance DD below shaft 318 to allow attachment portion 320 to extend through proximal spacer body 301 to engage universal broach distal body 802. Shaft 318 can be shortened to accommodate the increase in length of extension 833. In examples, distance DD can equal the height of proximal spacer body 301, which can equal distance D1 of FIGS. 2A and 2B. The bottom or distal surface of shaft 318 can rest on top of spokes 824A-824F of universal broach proximal body 801, thereby facilitating transmission of force from shaft 318 to universal broach distal body 802. This can facilitate insertion of universal broach distal body 802 as compared to universal broach 100 of FIGS. 4A-5B where most or all of the force from shaft 318 is transmitted through attachment portion 320.

Figure 34:
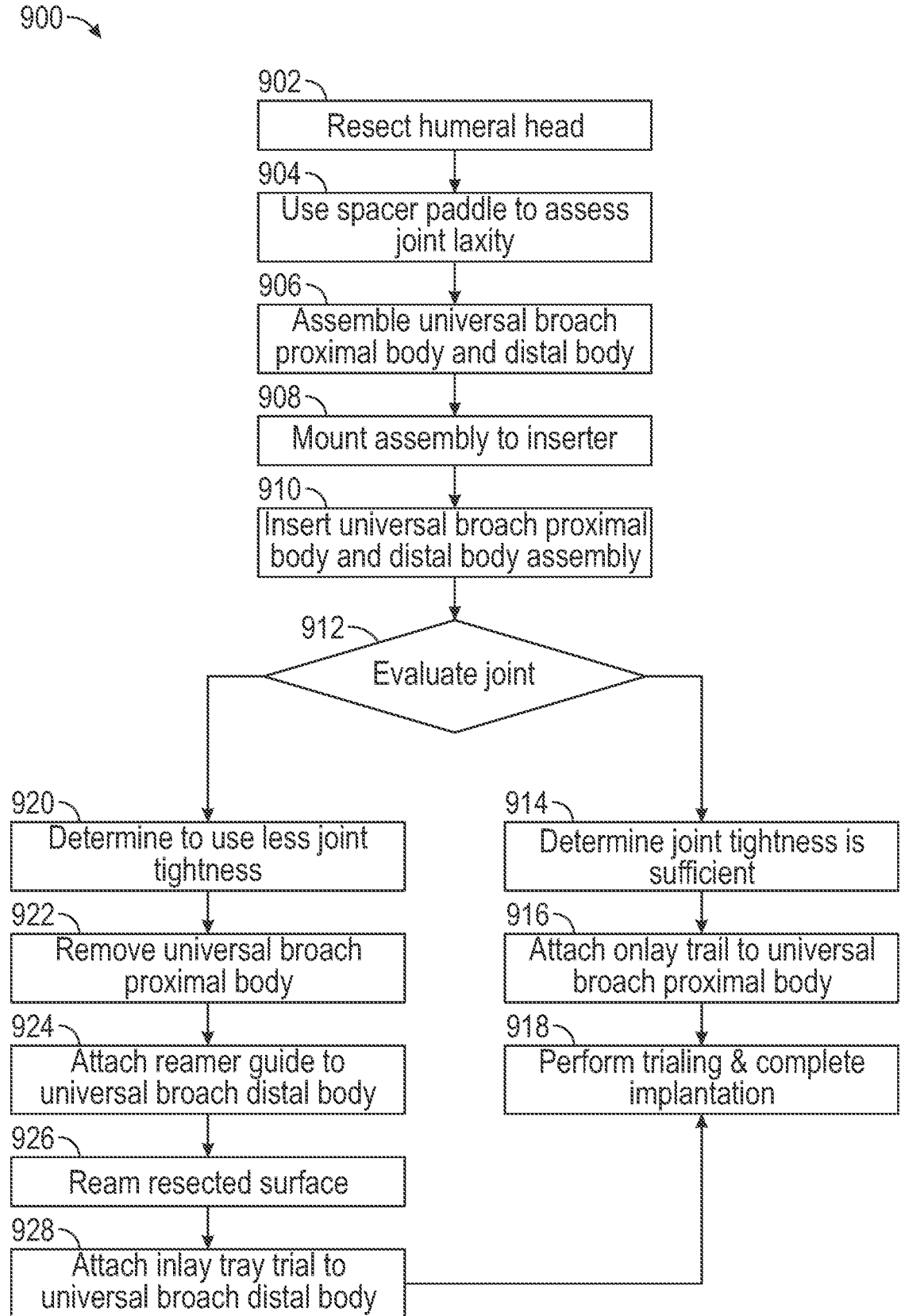
FIG. 34 is a line diagram illustrating operations of methods of the present disclosure relating to implanting inlay or onlay tray configurations using a universal broach proximal body and a universal broach distal body of the present disclosure.

FIG. 34 is a line diagram illustrating method 900 including operations 902-928 of the present disclosure relating to implanting inlay or onlay tray configurations using universal broach distal body 802 and universal broach proximal body 801 of the present disclosure. Method 900 can comprise operation 902 through operation 928 that describe various procedures for implanting a universal broach and determining the laxity of a shoulder joint in order to determine if an inlay tray trail component or an onlay tray trial component will or should be attached to the universal broach. In various examples, additional operations consistent with the devices, systems methods and operations described herein can be included. Likewise, some of operation 902-operation 928 can be omitted.

At operation 902, humeral bone 200 (FIG. 2A) can be resected to form resected surface 202. Resection of humeral bone 200 can be performed using conventional techniques. Resected surface 202 can comprise resected surface 850A of FIG. 26B and resected surface 850B of FIG. 27B.

At operation 904, a version of spacer 400 (FIG. 6A) not including attachment portion 408 can be inserted between the scapular bone and resected surface 850A or 850B of humeral bone 852A or 852B. The bottom surface of head 402 can be slid across resected surface 202 without interference. Thus, a surgeon can manipulate spacer 400 by sliding head 402 back and forth to ensure that a prosthetic head implant engages articulating surface 406 in order to evaluate the joint.

At operation 906, the tension or laxity of a shoulder joint can be evaluated, assessed or determined. The laxity of the joint, e.g., shoulder joint 700 of FIG. 13, can be determined by assessing the tension in the soft tissue holding the humeral bone on contact with or close proximity to the scapular bone. It is desirable to replicate the tension of a natural shoulder joint where the soft tissues hold the bones in engagement, but the joint is not too tight or difficult to move for the patient. Thus, if spacer 400 cannot fit between the humeral bone and the scapular bone, the soft tissue is holding the joint sufficiently tight such that a shorter (relative to extension beyond resected surface 202) or deeper (relative to insertion into resected surface 202) prosthetic implant can be used, such as an inlay tray. However, if spacer 400 can readily fit between the humeral bone and the scapular bone, this can be an indication that the soft tissue is not holding the joint sufficiently tight such that a taller (relative to extension beyond resected surface 202) or shallower (relative to insertion into resected surface 202) prosthetic implant can be used, such as an onlay tray.

At operation 908, universal broach proximal body 801 can be assembled with universal broach distal body 802. As discussed, pegs 828A and 828B can be inserted into ports 812A and 812B.

At operation 910, universal broach distal body 802 and universal broach proximal body 801 can be inserted into resected surface 850A or 850B using inserter 300 (FIGS. 32 and 33). Attachment portion 320 can pass through universal broach proximal body 801 to attach to socket 810 of universal broach distal body 802. The bottom of shaft 318 can be pushed against universal broach proximal body 801 to drive universal broach distal body 802 into bone. Inserter 300 can be released from universal broach distal body 802 to leave universal broach distal body 802 and proximal spacer body 301 disposed in the bone.

At operation 912, a surgeon can use information obtained at operation 904 to decide to use an inlay tray or an onlay tray. The surgeon can reevaluate the joint using spacer 400 to confirm if the previous assessment at operation 904 is acceptable, if desired.

At operation 914, a surgeon can determine that spacer 400 can readily fit between the humeral bone and the scapular bone. As such, the surgeon can determine that the soft tissue is not holding a component having the thickness of the spacer joint tight enough to replicate a natural joint. As such, the surgeon can determine that a taller or thicker (relative to joint gap height) humeral head build-up, e.g., prosthetic implant, can be used, such as onlay tray 206, if desired. For example, the tightness of the joint may be that either inlay or onlay trays may work, depending on construct of T1-T4.

At operation 916, the surgeon can attach onlay tray 206 (FIG. 2B) to universal broach proximal body 801 connected to universal broach distal body 802. Thus, attachment portion 216 of onlay tray 206 can be inserted into socket 822 of main body 820.

At operation 918, the surgeon can complete trialing of the joint using universal broach distal body 802, universal broach proximal body 801 and onlay tray 206 in order to build a final construct that will be implanted into the patient. For example, different sized prosthetic bearing components 230 can be attached to onlay tray 206 to determine the final joint laxity and the construct for the non-trialing implant or final prosthetic implant to be used.

At operation 920, a surgeon can determine that spacer 400 cannot readily fit between the humeral bone and the scapular bone. As such, the surgeon can determine that spacer 400 cannot fit between the humeral bone and the scapular bone, or cannot fit without using undue force. As such, the surgeon can determine that the soft tissue is holding the joint sufficiently tight such that a shorter or thinner (relative to joint gap height) humeral build-up, e.g., prosthetic implant, can be used such as inlay tray 250 (FIG. 3B), if desired. For example, the tightness of the joint may be that either inlay or onlay trays may work, depending on construct of T1-T4.

At operation 922, universal broach proximal body 801 can be separated from universal broach distal body 802. In examples, universal broach proximal body 801 can be removed manually. In examples, removal tool 860 (FIGS. 28-31) can be used.

At operation 924, a surgeon can attach reaming guide 500 (FIG. 7) to universal broach distal body 802. Attachment portion 504 of reaming guide 500 can be inserted into socket 810 of main body 803.

At operation 926, resected surface 850A or 850B can be reamed. Reamer 520 (FIG. 9) can be advanced over reaming guide 500 to engage reaming head 524 with resected surface 850A or 850B.

At operation 928, the surgeon can attach inlay tray 250 to universal broach distal body 802. Thus, reaming guide 500 can be removed from universal broach distal body 802 and attachment portion 258 of inlay tray 250 can be inserted into socket 810 of main body 803. Thereafter, the surgeon can complete trialing of the joint using universal broach distal body 802 and inlay tray 250 in order to build a final construct that will be implanted into the patient, such as at operation 918.

The systems, devices and methods discussed in the present application can be useful and provide advantages in the following ways:

1) The present subject matter can facilitate evaluation of the laxity or tension in a joint, such as a shoulder joint, for different types of implants before one or more bones of the joint are modified, such as in a way that makes the modified bone incompatible with at least one of the different types of implants. As such, premature and irreversible modification of bones can be avoided.

2) The present subject matter can reduce the amount of instrumentation involved in performing arthroplasty procedures by eliminating multiple broaches for inlay and onlay tray configurations, as well as eliminating trialing anchors for such configurations.

3) The present subject matter can reduce the amount of time to perform arthroplasty procedures by simplifying the arthroplasty process and the joint tension evaluation process. For example, a single resection can be used for both inlay and onlay trays and a single spacer device can be used to evaluate joint tension for inlay and onlay trays.

EXAMPLES

Example 1 is a broach for preparing a bone for receiving an anchor for a prosthetic implant, the broach comprising: a body comprising: a superior surface; and a socket extending into the superior surface; and a first anchoring component extending from the body, the first anchoring component comprising: a spoke extending laterally from the body; and a spoke tip extending proximally from the spoke above the superior surface.

In Example 2, the subject matter of Example 1 optionally includes wherein the first anchoring component comprises: a blade extending laterally from the body; and a wing extending circumferentially from the blade.

In Example 3, the subject matter of Example 2 optionally includes wherein the blade comprises: a proximal surface that extends arcuately upward from the superior surface; and a distal edge configured to cut bone matter.

In Example 4, the subject matter of any one or more of Examples 1-3 optionally include wherein the first anchoring component comprises one of a plurality of anchoring components extending laterally from the body.

In Example 5, the subject matter of Example 4 optionally includes wherein the plurality of anchoring components forms a bowl-shaped receptacle to accommodate a reamer.

Example 6 is a system for preparing a bone for receiving a prosthetic implant, the system comprising: a broach comprising: a body comprising a socket extending into a superior surface of the body; and an anchoring component extending from the body; a spacer comprising: an attachment component configured to attach to the socket; and a spacer body attached to the attachment component; an onlay implant comprising: a second attachment component configured to attach to the socket; a planar base attached to the second attachment component; and a first bearing component attached to the planar base; and an inlay implant comprising: a third attachment feature configured to attach to the socket; a bowl-shaped base attached to the third attachment feature; and a second bearing component attached to the bowl-shaped base; wherein the spacer body has a thickness that is equal to a maximum gap thickness of the inlay implant.

In Example 7, the subject matter of Example 6 optionally includes wherein the maximum gap thickness comprises a distance between a bottom of an articulating surface of the second bearing component and a bottom of the bowl-shaped base.

In Example 8, the subject matter of any one or more of Examples 6-7 optionally include wherein the bowl-shaped base is connectable to a plurality of different second bearing components each having a different thickness.

In Example 9, the subject matter of Example 8 optionally includes wherein the plurality of different second bearing components are also attachable to the planar base of the onlay implant.

In Example 10, the subject matter of any one or more of Examples 6-9 optionally include wherein: the onlay implant and the broach together form an onlay trialing device; and the inlay implant and the broach together form an inlay trialing device.

In Example 11, the subject matter of any one or more of Examples 6-10 optionally include an inserter device configured to insert the broach into bone a fixed distance.

In Example 12, the subject matter of any one or more of Examples 6-11 optionally include a reamer guide configured to attach to the socket of the broach; and a reamer configured to slide along the reamer guide, wherein the reamer comprises a reamer head configured to be advanced along the reamer guide to fit within a bowl-shaped receptacle formed by a superior surface of the broach.

Example 13 is a method of implanting a prosthetic component into a bone, the method comprising: inserting a broach into a resected surface of a first bone of a joint; attaching a spacer to the broach; positioning the spacer, while attached to the broach, into a space between the first bone and a second bone of the joint; determining to use an inlay tray or an onlay tray based on laxity of the joint with the spacer inserted therein; attaching the onlay tray to the broach if the joint is loose; and attaching the inlay tray to the broach if the joint is tight.

In Example 14, the subject matter of Example 13 optionally includes wherein attaching the inlay tray to the broach if the joint is tight comprises reaming the reseced surface of the bone.

In Example 15, the subject matter of Example 14 optionally includes wherein reaming the reseced surface of the bone comprises: attaching a reamer guide to the broach; and advancing a reamer over the reamer guide to ream the reseced surface, wherein the reamer is advanced into a bowl-shaped receptacle formed by a superior surface of the broach.

In Example 16, the subject matter of any one or more of Examples 13-15 optionally include wherein inserting the broach into the reseced surface of the first bone of the joint comprises inserting the broach a fixed distance below the reseced surface for both the inlay tray and the onlay tray.

In Example 17, the subject matter of Example 16 optionally includes wherein inserting the broach into the reseced surface of the first bone of the joint comprises: loading the broach into an inserter such that blades of the broach extend from the inserter; pushing the blades of the broach into bone matter of the first bone until the inserter contacts the first bone; and actuating the inserter to drive the broach further into the first bone to the fixed distance.

In Example 18, the subject matter of any one or more of Examples 13-17 optionally include wherein attaching the onlay tray to the broach if the joint is loose comprises positioning a bottom surface of the onlay tray against the reseced surface.

In Example 19, the subject matter of Example 18 optionally includes wherein the joint is loose if the spacer fits into the space between the first bone and the second bone.

In Example 20, the subject matter of any one or more of Examples 13-19 optionally include wherein attaching the inlay tray to the broach if the joint is tight comprises positioning a bottom surface of the inlay tray within the reseced surface.

In Example 21, the subject matter of Example 20 optionally includes wherein the joint is tight if the spacer does not fit into the space between the first bone and the second bone.

In Example 22, the subject matter of any one or more of Examples 13-21 optionally include adding one of a plurality of bearing components that each have a different thickness to the inlay tray to adjust laxity of the joint.

In Example 23, the subject matter of any one or more of Examples 13-22 optionally include adding one of a plurality of bearing components that each have a different thickness to the onlay tray to adjust laxity of the joint.

In Example 24, the subject matter of any one or more of Examples 13-23 optionally include wherein inserting the broach into the reseced surface of the first bone of the joint comprises: inserting a pin into the reseced surface; and reaming an initial bore into the reseced surface to receive a main body of the broach.

Example 25 is a system for preparing a bone for receiving an anchor for a prosthetic implant, the system comprising: a first distal broach component comprising: a first broach body; a first socket extending into a first superior surface of the first broach body; and a first plurality of cutting spokes extending radially from the first broach body, each of the first plurality of cutting spokes separated by an interval pattern; and a proximal broach component comprising: a spacer body configured to attach to the first superior surface of the first broach body; and a plurality of spacer spokes extending radially from the spacer body, each of the plurality of spacer spokes separated by the interval pattern.

In Example 26, the subject matter of Example 25 optionally includes a second distal broach component, the second distal broach component comprising: a second broach body; a second socket extending into a second superior surface of the second broach body; and a second plurality of cutting spokes extending radially from the second broach body, each of the second plurality of cutting spokes separated by the interval pattern; wherein at least some of the second plurality of cutting spokes is longer than each of the first plurality of cutting spokes.

In Example 27, the subject matter of any one or more of Examples 25-26 optionally include wherein: the first broach body comprises a first coupler; and the spacer body comprises a second coupler configured to mate with the first coupler.

In Example 28, the subject matter of any one or more of Examples 25-27 optionally include wherein: each of the first plurality of cutting spokes comprises: a spoke extending laterally from the first broach body; and a blade edge extending along the spoke.

In Example 29, the subject matter of Example 28 optionally includes wherein each of the first plurality of cutting spokes includes a spoke tip extending proximally from a cutting spoke above a superior surface of the first broach body and a radially extending surface extending flush with the spoke tip toward the first socket.

In Example 30, the subject matter of any one or more of Examples 25-29 optionally include an onlay implant comprising: a second attachment component configured to attach to the spacer body; a planar base attached to the second attachment component; and a first bearing component attached to the planar base; and an inlay implant comprising: a third attachment feature configured to attach to the first socket; a bowl-shaped base attached to the third attachment feature; and a second bearing component attached to the bowl-shaped base; wherein the spacer body has a thickness that is equal to a maximum gap thickness of the inlay implant.

In Example 31, the subject matter of Example 30 optionally includes a spacer paddle comprising a spacer body and a handle extending from the spacer body; wherein the spacer body has a thickness that is equal to a maximum gap thickness of the inlay implant.

In Example 32, the subject matter of any one or more of Examples 30-31 optionally include wherein the maximum gap thickness comprises a distance between a bottom of an articulating surface of the second bearing component and a bottom of the bowl-shaped base.

In Example 33, the subject matter of any one or more of Examples 30-32 optionally include wherein the bowl-shaped base is connectable to a plurality of different second bearing components each having a different thickness.

In Example 34, the subject matter of Example 33 optionally includes wherein the plurality of different second bearing components are also attachable to the planar base of the onlay implant.

In Example 35, the subject matter of any one or more of Examples 30-34 optionally include wherein: the onlay implant, the proximal broach component and the first distal broach component together form an onlay trialing device; and the inlay implant and the first distal broach component together form an inlay trialing device.

In Example 36, the subject matter of any one or more of Examples 30-35 optionally include an inserter device configured to insert the first distal broach component and the proximal broach component into bone a fixed distance.

In Example 37, the subject matter of any one or more of Examples 30-36 optionally include a reamer guide configured to attach to the first socket of the first distal broach component; and a reamer configured to slide along the reamer guide, wherein the reamer comprises a reamer head configured to be advanced along the reamer guide to fit within a bowl-shaped receptacle formed by a superior surface of the first distal broach component.

In Example 38, the subject matter of any one or more of Examples 30-37 optionally include a removal tool comprising: a knob; a shaft extending from the knob; and a threaded tip configured to threadedly engage the spacer body of the proximal broach component.

Example 39 is a method of implanting a prosthetic component into a bone, the method comprising: resecting surface of a first bone joint; inserting a spacer paddle to assess laxity of the first bone joint; assembling a proximal spacer body with a distal broach body to form a broach assembly; inserting the broach assembly into a resected surface of a first bone of a joint; determining to use an inlay tray or an onlay tray based on the assessed laxity of the first bone joint; attaching the onlay tray to the broach assembly if the joint is loose; and attaching the inlay tray to the distal broach body if the joint is tight.

In Example 40, the subject matter of Example 39 optionally includes wherein attaching the inlay tray to the distal broach body if the joint is tight comprises: removing the proximal spacer body form the distal broach body if the joint is tight; and reaming the resected surface of the bone.

In Example 41, the subject matter of Example 40 optionally includes wherein reaming the resected surface of the bone comprises: attaching a reamer guide to the distal broach body; and advancing a reamer over the reamer guide to ream the resected surface, wherein the reamer is advanced into a bowl-shaped receptacle formed by a superior surface of the distal broach body.

In Example 42, the subject matter of any one or more of Examples 39-41 optionally include wherein inserting the broach assembly into the resected surface of the first bone of the joint comprises inserting the distal broach body a fixed distance below the resected surface for both the inlay tray and the onlay tray, the fixed distance equaling a height of the proximal spacer body.

In Example 43, the subject matter of Example 42 optionally includes wherein inserting the broach assembly into the resected surface of the first bone of the joint comprises: loading the broach assembly into an inserter such that blades of the distal broach body extend from the inserter; pushing the blades of the distal broach body into bone matter of the first bone until the inserter contacts the first bone; and actuating the inserter to drive the distal broach body further into the first bone to the fixed distance, thereby positioning the proximal spacer body within bone.

In Example 44, the subject matter of any one or more of Examples 39-43 optionally include wherein attaching the onlay tray to the broach assembly if the joint is loose comprises positioning a bottom surface of the onlay tray against the resected surface.

In Example 45, the subject matter of Example 44 optionally includes wherein the joint is loose if the spacer paddle fits into a space between the first bone and a second bone forming the first bone joint.

In Example 46, the subject matter of any one or more of Examples 39-45 optionally include wherein attaching the inlay tray to the distal broach body if the joint is tight comprises positioning a bottom surface of the inlay tray within the resected surface.

In Example 47, the subject matter of Example 46 optionally includes wherein the joint is tight if the spacer paddle does not fit into a space between the first bone and a second bone forming the first bone joint.

In Example 48, the subject matter of any one or more of Examples 39-47 optionally include adding one of a plurality of bearing components that each have a different thickness to the inlay tray to adjust laxity of the joint.

In Example 49, the subject matter of any one or more of Examples 39-48 optionally include adding one of a plurality of bearing components that each have a different thickness to the onlay tray to adjust laxity of the joint.

In Example 50, the subject matter of any one or more of Examples 39-49 optionally include wherein inserting the broach assembly into the resected surface of the first bone of the joint comprises: inserting a pin into the resected surface; and reaming an initial bore into the resected surface to receive a main body of the distal broach body.

Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for preparing a bone for receiving a first anchor for a prosthetic implant, the system comprising:
    a first distal broach component comprising:
        a first broach body comprising a first superior surface;
        a first socket defined by the first broach body, the first socket extending into the first superior surface of the first broach body; and
        a first plurality of cutting spokes extending radially from the first broach body, each of the first plurality of cutting spokes separated by a first spacing such that an interval pattern is formed between adjacent cutting spokes; and
    a proximal broach component comprising:
        a spacer body comprising an inferior spacer surface configured to attach to the first superior surface of the first broach body such that the first broach body sits superior of the spacer body; and
        a plurality of spacer spokes extending radially from the spacer body, each of the plurality of spacer spokes separated by a second spacing equivalent to the interval pattern, the plurality of spacer spokes configured to be positioned superior of the first plurality of cutting spokes when the inferior spacer surface is attached to the first superior surface.

2. The system of claim 1, further comprising a second distal broach component different than the first distal broach component configured to prepare the bone for a second anchor, the second distal broach component configured for use with the proximal broach component alternatively to the first distal broach component, the second distal broach component comprising:
    a second broach body comprising a second superior surface;
    a second socket defined by the second broach body, the second socket extending into the second superior surface of the second broach body; and
    a second plurality of cutting spokes extending radially from the second broach body, each of the second plurality of cutting spokes separated by a third spacing equivalent to the interval pattern;
    wherein at least some of the second plurality of cutting spokes is longer than each of the first plurality of cutting spokes.

3. The system of claim 1, wherein:
    the first broach body comprises a first coupler, the first coupler comprising a pair of sockets extending into the first superior surface; and the spacer body comprises a second coupler configured to mate with the first coupler, the second coupler comprising a pair of pegs extending from the inferior spacer surface;
    wherein the pair of pegs configured to extend into the pair of sockets.

4. The system of claim 1, wherein:
    each of the first plurality of cutting spokes comprises:
        a spoke extending laterally from the first broach body; and
        a blade edge extending along the spoke;
    wherein each of the first plurality of cutting spokes includes a spoke tip extending superiorly from a cutting spoke above a superior surface of the first broach body and a radially extending surface extending flush with the spoke tip toward the first socket.

5. The system of claim 1, further comprising:
    an onlay implant comprising:
        a second attachment component configured to attach to the spacer body;
        a planar base attached to the second attachment component; and
        a first bearing component attached to the planar base; and
    an inlay implant comprising:
        a third attachment feature configured to attach to the first socket;
        a bowl-shaped base attached to the third attachment feature; and
        a second bearing component attached to the bowl-shaped base;
    wherein the spacer body has a thickness that is equal to a maximum gap thickness of the inlay implant.

6. The system of claim 5, further comprising:
    a spacer paddle comprising a spacer body and a handle extending from the spacer body;
    wherein the spacer body has a thickness that is equal to a maximum gap thickness of the inlay implant; and
    wherein the maximum gap thickness comprises a distance between a bottom of an articulating surface of the second bearing component and a bottom of the bowl-shaped base.

7. The system of claim 5, wherein the bowl-shaped base is connectable to a plurality of different second bearing components each having a different thickness, wherein plurality of different second bearing components are also attachable to the planar base of the onlay implant.

8. The system of claim 5, wherein:
    the onlay implant, the proximal broach component and the first distal broach component together form an onlay trialing device; and
    the inlay implant and the first distal broach component together form an inlay trialing device.

9. The system of claim 5, further comprising:
    an inserter device configured to insert the first distal broach component and the proximal broach component into bone a fixed distance; and
    a removal tool comprising:
        a knob;
        a shaft extending from the knob; and
        a threaded tip configured to threadedly engage the spacer body of the proximal broach component.

10. The system of claim 5, further comprising:
    a reamer guide configured to attach to the first socket of the first distal broach component; and
    a reamer configured to slide along the reamer guide, wherein the reamer comprises a reamer head configured to be advanced along the reamer guide to fit within a bowl-shaped receptacle formed by a superior surface of the first distal broach component.

11. A system for preparing a bone for receiving an anchor for a prosthetic implant, the system comprising:

a first distal broach component comprising:

a first broach body comprising a first superior surface;

a first socket defined by the first broach body, the first socket extending into the first superior surface of the first broach body; and a first plurality of cutting spokes extending radially from the first broach body, each of the first plurality of cutting spokes separated by a first spacing such that an interval pattern is formed between adjacent cutting spokes;

a proximal broach component comprising:

a spacer body configured to attach to the first superior surface of the first broach body; and a plurality of spacer spokes extending radially from the spacer body, each of the plurality of spacer spokes separated by a second spacing equivalent to the interval pattern;

an onlay implant comprising:

a second attachment component configured to attach to the spacer body;

a planar base attached to the second attachment component; and a first bearing component attached to the planar base; and an inlay implant comprising:

a third attachment feature configured to attach to the first socket;

a bowl-shaped base attached to the third attachment feature; and a second bearing component attached to the bowl-shaped base;

wherein the spacer body has a thickness that is equal to a maximum gap thickness of the inlay implant.

12. A system for preparing a bone for receiving a first anchor for a prosthetic implant, the system comprising:

a first distal broach component comprising:

a first broach body comprising a first superior surface;

a first socket defined by the first broach body, the first socket extending into the first superior surface of the first broach body; and a first plurality of cutting spokes extending radially from the first broach body, each of the first plurality of cutting spokes separated by a first spacing such that an interval pattern is formed between adjacent cutting spokes;

a proximal broach component comprising:

a spacer body configured to attach to the first superior surface of the first broach body; and a plurality of spacer spokes extending radially from the spacer body, each of the plurality of spacer spokes separated by a second spacing equivalent to the interval pattern; and a second distal broach component different than the first distal broach component configured to prepare the bone for a second anchor, the second distal broach component configured for use with the proximal broach component alternatively to the first distal broach component, the second distal broach component comprising:

a second broach body comprising a second superior surface;

a second socket defined by the second broach body, the second socket extending into the second superior surface of the second broach body; and a second plurality of cutting spokes extending radially from the second broach body, each of the second plurality of cutting spokes separated by a third spacing equivalent to the interval pattern;

wherein at least some of the second plurality of cutting spokes is longer than each of the first plurality of cutting spokes.

\*    \*    \*    \*    \*